US009228192B2

(12) United States Patent
Giritch et al.

(10) Patent No.: US 9,228,192 B2
(45) Date of Patent: Jan. 5, 2016

(54) PLANT TRANSFORMATION WITH IN VIVO ASSEMBLY OF A SEQUENCE OF INTEREST USING A SITE-SPECIFIC RECOMBINASE

(75) Inventors: Anatoly Giritch, Halle/Saale (DE); Serik Eliby, Halle/Saale (DE); Sylvestre Marillonnet, Halle/Saale (DE); Victor Klimyuk, Halle/Saale (DE); Yuri Gleba, Halle/Saale (DE)

(73) Assignee: BAYER CROPSCIENCE N.V., Diegem (BE)

( * ) Notice: Subject to any disclaimer, the term of this patent is extended or adjusted under 35 U.S.C. 154(b) by 2205 days.

(21) Appl. No.: 10/544,135

(22) PCT Filed: Jan. 30, 2004

(86) PCT No.: PCT/EP2004/000892
§ 371 (c)(1),
(2), (4) Date: Aug. 23, 2005

(87) PCT Pub. No.: WO2004/067749
PCT Pub. Date: Aug. 12, 2004

(65) Prior Publication Data
US 2009/0265814 A1    Oct. 22, 2009

(30) Foreign Application Priority Data
Jan. 31, 2003  (DE) .................................. 103 03 937

(51) Int. Cl.
*A01H 1/00*      (2006.01)
*C12N 15/82*     (2006.01)
*C12N 15/00*     (2006.01)

(52) U.S. Cl.
CPC .................................. *C12N 15/8205* (2013.01)

(58) Field of Classification Search
USPC ......... 435/462, 468, 183; 530/370; 536/23, 2, 536/6; 800/278, 288, 295
See application file for complete search history.

(56) References Cited

U.S. PATENT DOCUMENTS

| | | | | |
|---|---|---|---|---|
| 5,501,967 | A * | 3/1996 | Offringa et al. ............... | 435/469 |
| 6,376,745 | B1 * | 4/2002 | Atabekov et al. ............. | 800/278 |
| 6,413,777 | B1 * | 7/2002 | Reff et al. ..................... | 435/463 |
| 6,531,316 | B1 | 3/2003 | Patten et al. | |
| 6,566,584 | B1 | 5/2003 | Coughlan | |
| 6,632,980 | B1 * | 10/2003 | Yadav et al. ................... | 800/278 |
| 7,112,721 | B2 * | 9/2006 | Fabijanski et al. ............ | 800/294 |
| 7,267,979 | B2 | 9/2007 | Yadav et al. | |
| 2005/0066384 | A1 * | 3/2005 | Klimyuk et al. .............. | 800/278 |
| 2007/0124831 | A1 | 5/2007 | Giritch et al. | |

FOREIGN PATENT DOCUMENTS

| | | |
|---|---|---|
| WO | WO 99/55851 | 11/1999 |
| WO | WO 02/081711 A1 | 10/2002 |
| WO | WO 02/088369 A1 | 11/2002 |
| WO | WO 02/097080 A2 | 12/2002 |

OTHER PUBLICATIONS

Segall. Site-specific Recombination. 2002. eLS. 1-8.*
Bioresearch Online. Gateway cloning technology—A universal cloning system. Dec. 10, 1999. http://www.bioresearchonline.com/doc/gateway-cloning-technologya-universal-cloning-0001.*
De Groot, M., et al., "Mechanisms of Intermolecular Homologous Recombination in Plants as Studied with Single- and Double-Stranded DNA Molecules," *Nucleic Acids Research*, 1992, pp. 2785-2794, vol. 20, No. 11, Oxford University Press.
Offringa, R., et al., "Extrachromosomal Homologous Recombination and Gene Targeting in Plant Cells After *Agrobacterium* Mediated Transformation," *EMBO Journal*, 1990, pp. 3077-3084, vol. 9, No. 10, Oxford University Press.
U.S. Appl. No. 10/545,665, filed Oct. 13, 2005, Giritch et al.
Bilang, R., et al., "Single-Stranded DNA as a Recombination Substrate in Plants as Assessed by Stable and Transient Recombination Assays," *Molecular and Cellular Biology*, 1992, pp. 329-336, vol. 12(1).
Debuck, S., et al., "The DNA sequences of T-DNA junctions suggest that complex T-DNA loci are formed by a recombination process resembling T-DNA integration," *The Plant Journal*, 1999, pp. 295-304, vol. 20(3).
De Neve, M, et al., "T-DNA integration patterns in co-transformed plant cells suggest that T-DNA repeats originate from co-integration of separate T-DNAs," *The Plant Journal*, 1997, pp. 15-29, vol. 11(1).
Deshpande, N. et al., "The atpF group-II intron-containing gene from spinach chloroplasts is not spliced in transgenic *Chlamydomonas* chloroplasts," *Curr. Genet.*, 1995, pp. 122-127, vol. 28.
Komari, T., et al., "Vectors carrying two separate T-DNAs for co-transformation of higher plants mediated by *Agrobacterium tumefaciens* and segregation of transformants free from selection markers," *The Plant Journal*, 1996, pp. 165-174, vol. 10(1).
Krizkova, L., et al., "Direct repeats of T-DNA integrated in tobacco chromosome: characterization of junction regions," *The Plant Journal*, 1998, pp. 673-680, vol. 16(6).

(Continued)

*Primary Examiner* — Phuong Bui
(74) *Attorney, Agent, or Firm* — Williams Mullen, PC; David M. Saravitz

(57) ABSTRACT

A process of producing transgenic plants or plant cells stably transformed on a chromosome with a DNA sequence of interest capable of expressing a function of interest, said process comprising (a) providing plant cells or plants with at least two different vectors that are adapted to recombine with each other between site-specific recombination sites compatible with a site-specific recombinase that is also provided in order to produce a non-replicating recombination product containing said DNA sequence of interest, (ii) said at least two different vectors are adapted for integrating said DNA sequence of interest into said chromosome, (iii) said DNA sequence of interest contains sequence portions from at least two of said at least two different vectors, said sequence portions being necessary for expressing said function of interest from said DNA sequence of interest; and (b) selecting plants or plant cells expressing said function of interest.

21 Claims, 20 Drawing Sheets

(56) References Cited

OTHER PUBLICATIONS

Paszkowski, J., et al., "Expression in transgenic tobacco of the bacterial neomycin phosphotransferase gene modified by intron insertions of various sizes," *Plant Molecular Biology*, 1992, pp. 825-836, vol. 19.

Smith, N., et al., "Total silencing by intron-spliced hairpin RNAs," *Nature*, 2000, pp. 319-320, vol. 407.

Zhao, X., et al., "T-DNA recombination and replication in maize cells," *The Plant Journal*, 2003, pp. 149-159, vol. 33.

Hoa, T.T.C. et al., "Cre/*lox* site-specific recombination controls the excision of a transgene from the rice genome," *Theor Appl Genet*, (2002) vol. 104, pp. 518-525.

Köhler et al., "*Trans*-splicing Ribozymes for Targeted Gene Delivery," *J. Mol. Biol.*, 1999, vol. 285, pp. 1935-1950.

Lewin, Benjamin, Chapter 33 "Recombination of DNA," *Genes V*, 1994, p. 967, Oxford University Press, Walton Street, Oxford OX26DP.

De Block, M. and Debrouwer, D., "Two T-DNA's co-transformed in *Brassica napus* by a double *Agrobacterium tumefaciens* infection are mainly integrated at the same locus," *Theor Appl Genet*, 1991, vol. 82, pp. 257-263.

Ghosh, K., and G. D. Van Duyne, "Cre-*loxP* biochemistry," *Methods*, 2002, pp. 374-383, vol. 28, Elsevier Science (USA).

Ray, A., and M. Langer, "Homologous recombination: ends as the means," *TRENDS in Plant Science*, Oct. 2002, pp. 435-440, vol. 7(10), Elsevier Science Ltd.

Zupan, et al., "The transfer of DNA from *Agrobacterium tumefaciens* into plants: a feast of fundamental insights," *The Plant Journal*, 2000, pp. 11-28, vol. 23(1), Blackwell Science Ltd.

Craig, Nancy L, "The Mechanism of Conservative Site-Specific Recomination", Annual Review of Genetics, Dec. 1988, vol. 22, pp. 77-105.

Camerini-Otero, Daniel R. "Homologous Recombination Proteins in Prokaryotes and Eukaryotes", Annual Review of Genetics, Feb. 1995, vol. 29, pp. 509-552.

Srivastava Visha et al: "Biolistic mediated site-specific integration in rice" Molecular Breeding, 2001, vol. 8, No. 4, pp. 345-350.

\* cited by examiner

PLANT TRANSFORMATION WITH IN VIVO ASSEMBLY OF A SEQUENCE OF INTEREST USING A SITE-SPECIFIC RECOMBINASE

FIELD OF THE INVENTION

The present invention relates to a process of producing transgenic plants transformed on a chromosome. Further the invention relates to a process of screening nucleotide sequences for a desired phenotype in plants. The invention also relates to transgenic plants and to libraries of plants or plant seeds obtained or obtainable according to the processes of the invention. Further, the invention relates to vectors for these processes and to plants or plant cells transformed therewith.

BACKGROUND OF THE INVENTION

Currently used methods of stable plant transformation usually employ direct (microprojectile bombardment, electroporation or PEG-mediated treatment of protoplasts, for review see: Gelvin, S. B., 1998, *Curr. Opin. Biotechnol.*, 9, 227-232; Hansen & Wright, 1999, *Trends Plant Sci.*, 4, 226-231) or *Agrobacterium*-mediated delivery of pre-engineered DNA fragment(s) of interest into plant cells. Manipulations with said DNA vectors in planta are restricted to simplifying the resolution of complex integration patterns (U.S. Pat. No. 6,114,600; Srivastava & Ow, 2001, *Plant Mol Biol.*, 46, 561-566; Srivastava et al., 1999, *Proc. Natl. Acad. Sci. USA*, 96, 11117-11121) or removal of auxiliary DNA sequences from vectors stably integrated into chromosomal DNA. The methods of stable *Agrobacterium*-mediated integration of T-DNA regions within plant cells use whole desired DNA fragment flanked with left (LB) and right (RB) border sequences necessary for T-DNA transfer and integration into the host chromosomal DNA (U.S. Pat. No. 4,940,838; U.S. Pat. No. 5,464,763; EP0224287; U.S. Pat. No. 6,051,757; U.S. Pat. No. 5,731,179; WO9400977; EP0672752). In most cases, the approaches are directed to the integration of one specific T-DNA region into the chromosomal DNA. Also, co-integration of two or more different T-DNA regions was tried (U.S. Pat. No. 4,658,082). The latter approach is used for segregating different T-DNAs in progeny for various purposes. For example, Komari and colleagues (U.S. Pat. No. 5,731,179) describe a method of simultaneously transforming plant cells with two T-DNAs, one carrying a selectable marker functional in plants, while another T-DNA contains a desired DNA fragment to be introduced into plant cells.

In general, the DNA regions designed for stable integration into plant cells are pre-engineered in vitro by employing standard molecular biology techniques (Sambrook, Fritsch & Maniatis, 1989, Molecular cloning: A laboratory manual, 2nd ed. Cold Spring Harbor, N.Y.: CSH Laboratory Press). Also, in vivo engineering in bacterial cells is used, for example in order to assemble the binary vector with the help of homologous recombination (U.S. Pat. No. 5,731,179). Manipulations with T-DNA in planta are restricted to T-DNA regions pre-integrated into a chromosome like removing certain sequences from T-DNA, e.g. sequences encoding selectable markers including morphological abnormality induction genes. The removal of unwanted DNA fragments from T-DNA regions occurs either with the help of site-specific recombination (WO9742334; Endo et al., 2002, *Plant J.*, 30, 115-122) or by means of transposition (U.S. Pat. No. 5,792,924).

Site-specific recombination has been used for removing auxiliary sequences from T-DNA regions. Although site-specific recombinase/integrase-mediated DNA excision is more efficient than integration, the selection for excision events is a necessity, which leads to an additional step of tissue culture or screening of progeny for desired recombination events. In summary, all processes of manipulation with T-DNAs stably integrated into plant chromosomes are time-consuming, unflexible, and in general restricted to simple excision (with less efficiency—to integration) of desired DNA fragments. In addition, these processes are usually very limited in combinatorial diversity, as they are restricted to simple manipulations with a limited number of known genes and regulatory elements.

Offringa et al. (EMBO J. (1990), 9, 3077-3084) have described an extrachromosomal homologous recombination event between two *Agrobacterium*-delivered T-DNAs in plant cells followed by integration of the recombination product into nuclear DNA. The extrachromosomal homologous recombination efficiency between the co-delivered T-DNAs in the plant cell was however too low to have practical applications for vector engineering in vivo and was therefore used as control experiment in scientific studies of the mechanism of homologous recombination in plants (Offringa et al., 1990, *EMBO J.*, 9, 3077-3084; Tinland et al., 1994, *Proc. Natl. Acad. Sci. USA*, 91, 8000-8004; Puchta et al., 1996, *Proc. Natl. Acad. Sci. USA*, 93, 5055-5060). The frequency of homologous recombination followed by integration into chromosomal DNA was approximately 1% of the plant co-transformation frequency with two T-DNAs (Offringa et al., 1990, *EMBO J.*, 9, 3077-3084; Tinland et al., 1994, *Proc. Natl. Acad. Sci. USA*, 91, 8000-8004; Puchta et al., 1996, *Proc. Natl. Acad. Sci. USA*, 93, 5055-5060). Due to the low overall efficiency of this process, practical applications of this method have not been developed.

The frequency of targeted integration of transiently delivered T-DNA into a pre-engineered loxP site in plants is also very low. For example, Vergunst and colleagues (1998, *Nucl. Acids Res.*, 26, 2729-2734) demonstrated that the frequency of Cre-mediated site-specific integration of an *Agrobacterium*-delivered T-DNA fragment of interest into a genomic T-DNA region with a loxP site is within the range of 1.2-2.3% of the number of random integration events. Due to this low efficiency, such integration processes require an additional selection round and the use of tissue culture to recover the cells carrying recombination events. In contrast to that, the frequency of chromosomal double-stranded DNA rearrangements with the help of site-specific recombinases is significantly higher and occurs in 29-100% of all plant germ cells (Zuo et al., 2001, *Nature Biotechnol.*, 19, 157-161; Luo et al., *Plant J.*, 23, 423-430). This is not surprising, as site-specific integrases/recombinases require double stranded DNA substrate for recognition of recombination sites and performing the reaction of site-specific recombination (Panigrahi et al., 1992, *Nucleic Acids Res.*, 20, 5927-5935; Martin et al., 2002, *J. Mol. Biol.*, 19, 107-127; Thorpe et al., 2000, *Mol. Microbiol.*, 38, 232-241).

All data mentioned above suggest that T-DNA transiently delivered into the plant cell is a poor substrate for site-specific recombinases.

In a previous invention, we have overcome the above-described low efficiency by site-specific recombination-mediated assembly of RNA-viral amplicons (WO02/088369). The assembled viral amplicons were capable of strong autonomous amplification, cell-to-cell and systemic movement and, therefore, could strongly amplify the rare recombination events. Said viral amplicons were assembled in planta from two or more vectors by recombinase-mediated site-specific recombination and contained a gene of interest to be expressed transiently with the aim of achieving the strongest possible expression of the gene of interest throughout a plant that was infected by said vectors. However, expression of gene of interest was transient; stable transformation of plant chromosomes for stable and inheritable expression of a gene of interest was not addressed.

For many applications, the methods described in WO02/088369 can, however, not be used due to the following problems: Amplification and spread of the viral amplicon leads to viral disease symptoms that compromise plant health. Therefore, these methods cannot be used for gene function determination (functional genomics) since disease symptoms frequently obscure the function of a gene to be determined or prevent expression of the function to be determined. Further, expression of a gene of interest from an amplicon gives rise to unnaturally high expression levels leading to phenotypes different from the natural phenotype of that gene, perhaps due to unnatural interactions with functions of native genes of that plant.

Therefore, it is an object of the invention to provide an efficient, rapid and highly versatile process for transforming a plant or plant cells on a chromosome, notably a nuclear chromosome, whereby genetically stable transgenic plants or plant cells may be produced. It is another object of the invention to provide a process of producing transgenic plants transformed on a chromosome, whereby (e.g. for reducing cloning work) the DNA sequences to be integrated in said chromosome can be engineered in planta. It is a further object to provide a process of stably transforming plants or plant cells on a chromosome with a DNA sequence of interest having toxic effects on bacteria normally used for cloning said DNA sequence of interest. It is another object of the invention to provide a process of genetic transformation of plant nuclear DNA, which allows for screening for an optimal expression unit of a gene of interest. It is a further object to provide a process of stably transforming plants or plant cells on a chromosome, whereby vectors can be used in a modular fashion, for reducing the cloning work and the overall size of the vector molecules. It is another object of the invention to provide a process of stably transforming plants or plant cells on a chromosome, whereby said process allows screening of DNA libraries for desired functions in plants. It is further object of the invention to provide an in planta process of shuffling genetic elements/gene fragments, whereby said process is linked with a process of stably transforming plants or plant cells with a DNA sequence of interest resulting from said shuffling.

GENERAL DESCRIPTION OF THE INVENTION

The above objects are achieved by a process of producing transgenic plants or plant cells transformed on a chromosome with a DNA sequence of interest and capable of expressing a function of interest from said DNA sequence of interest, said process comprising:
(a) providing plant cells or plants with at least two different vectors, whereby
   (i) said at least two different vectors are adapted to recombine with each other by site-specific recombination in said plant cells for producing a non-replicating recombination product containing said DNA sequence of interest,
   (ii) said at least two different vectors are adapted for integrating said DNA sequence of interest into said chromosome,
   (iii) said DNA sequence of interest contains sequence portions from at least two of said at least two different vectors, said sequence portions being necessary for expressing said function of interest from said DNA sequence of interest; and
(b) selecting plants or plant cells expressing said function of interest.

The invention further provides transgenic plants or parts thereof (like seeds) produced or producible by the process of the invention. Further, libraries of plants or plant seeds obtained or obtainable by this process are provided. The process of the invention has many important applications, among which its use in DNA library screening, gene function analysis and functional genomics, and directed evolution including gene shuffling may be mentioned. Moreover, complex and/or large DNA sequences of interest to be introduced in a plant chromosome can be assembled in planta from smaller precursors (see FIG. 12). The process of the invention can, however, also be used for introducing a gene to be expressed in a chromosome of a plant cell or plant. In an important embodiment, all genes and/or coding sequences and/or expressible sequences of said DNA sequence of interest integrated into a chromosome are of plant origin, whereby no unnatural sequences can be outcrossed from the transgenic plants of the invention to other organisms.

The inventors of this invention have surprisingly found that transiently delivered T-DNA can be efficiently used for in planta engineering of a sequence of interest for integration into a chromosome. Preferably, the efficiency of achieving stable integration events is comparable to that for a standard *Agrobacterium*-mediated transformation. The reason for this unexpectedly high efficiency has not yet been elucidated. The overall process of the invention is of sufficient efficiency for enabling routine applications of the process of the invention. For example, screening of DNA libraries for a useful trait can for the first time be performed in planta with a low danger of missing library members that are not compatible with the prokaryotic systems used for cloning in traditional approaches. This allows to combine the processes of vector engineering (e.g. for functional genomics or directed evolution purposes) with the creation of stable transformants, thus significantly speeding up the process of screening for desired combinations of genetic elements under test.

The process of the invention allows to produce transgenic plants or plant cells that are stably transformed on a chromosome with a DNA sequence of interest, whereby said DNA sequence of interest derives from at least two different vectors. Stable transformation of a chromosome means integration of said DNA sequence of interest in said chromosome such that said DNA sequence of interest is replicated together with said chromosome. Preferably, said DNA sequence of interest can be inherited during cell division and organism reproduction for several generations.

In step (a) of the process of the invention, a plant or plant cells are provided with at least two different vectors, whereby said at least two different vectors are as defined below. Herein, "different vectors" means preferably "different types of vectors". Plant cells may be provided with said at least two different vectors in issue culture, notably in tissue culture of plant cell protoplasts. Further, explants (e.g. root explants, leaf discs) of a plant may be provided with said at least two different vectors. Moreover, entire plants or parts of entire plants may be provided with said vectors.

Said providing of step (a) may be performed by a direct transformation method (e.g. particle bombardment, electroporation, PEG-mediated transformation of protoplasts) or by *Agrobacterium*-mediated T-DNA delivery, whereby *Agrobacterium*-mediated T-DNA delivery is preferred due to its superior efficiency in the process of the invention. Said at least two different vectors may be provided to said plant or said plant cells consecutively. However, said providing with said at least two different vectors is not separated by a cycle of reproduction of the transformed plant or a cycle of regeneration of a plant transformed with one vector followed by transformation with another vector of said at least two different vectors. Preferably, said plant or said plant cells are provided with said at least two vectors in a one-step procedure. In the case of direct vector delivery, this means that mixtures of said vectors are preferably used in step (a). In the case of *Agrobacterium*-mediated T-DNA delivery, mixtures of *Agrobacterium* strains (or cells) are preferably used, whereby each strain or cell contains a different Ti-plasmid, each Ti-plasmid containing a different vector of said at least two different vectors. Most preferably, a particular *Agrobacterium* strain contains one type of Ti-plasmid having a certain vector, but no Ti-plasmids containing a different vector, whereas another *Agrobacterium* strain contains another type of Ti-plasmid having another type of vector but not Ti-plasmids containing a different vector. I.e. no *Agrobacterium* cell provides more than one type of said at least two different vectors. Providing said plant cells or plants in a one step procedure with said vectors, notably simultaneously, is work-efficient and gives a good overall efficiency of the process of the invention.

After having provided said plants or said plant cells with said at least two different vectors, a recombination product containing said DNA sequence of interest is formed within plant cells by site-specific recombination between at least two of said at least two different vectors. For this purpose, each of said at least two different vectors is adapted to recombine with at least one other vector of said at least two different vectors. If three or more different types of vectors are used, each may be adapted to recombine with every other vector. For some applications, it may however be sufficient if each vector of said at least two different vectors is adapted to recombine with one other vectors of said at least two different vectors.

Said adaption to recombination may be achieved by including site-specific recombination site(s) on said vectors for enabling said site-specific recombinations. Preferably, said site-specific recombination is adapted such that the reversion (i.e. the back reaction) of said site-specific recombination occurs with low probability. This may e.g. be achieved by providing the enzyme for said recombination transiently (e.g. by rendering the recombinase gene non-expressible by said recombination). More preferably, a site-specific recombinase/recombination site system is chosen that performs irreversible recombinations, which may be achieved by using an integrase together with the appropriate recombination sites. Integrases use two different recombination sites (like AttP and AttB in the case of phi C31 integrase), which allows directed and irreversible recombination.

A gene of a site-specific recombinase or integrase compatible with the selected site-specific recombination sites should be provided (e.g. with one of said at least two different. vectors) such that said recombinase or integrase can be expressed. Preferably, said recombinase or integrase gene is provided on one of said at least two different vectors such that (i) it can be expressed prior to the site-specific recombination event and (ii) such that its expression is blocked after said recombination has occurred. Alternatively, the plant cells or plants provided with said at least two different vectors in step (a) may already contain and express a gene coding for a recombinase or integrase.

By said site-specific recombination between said at least two different vectors, one or more different recombination products may be formed, whereby at least one recombination product contains said DNA sequence of interest. A recombination product containing said DNA sequence of interest is non-replicating in order to avoid disease symptoms due to strong replication of said recombination product. Preferably, all recombination products are non-replicating. Non-replicating means that the recombination product is not a viral nucleic acid capable of autonomous replication, since this generally produces disease symptoms that are incompatible with many applications like gene function determinations. Most preferably, said recombination product does not encode a functional viral replicase supporting replication of the recombination product.

Said DNA sequence of interest contains sequence portions from at least two of said at least two different vectors, whereby said sequence portions are necessary for expressing said function of interest from said DNA sequence of interest. While the DNA sequence of interest may contain three or more sequence portions of three or more different vectors, the DNA sequence of interest preferably contains two sequence portions of two vectors of said at least two different vectors. Recombination between said at least two different vectors may result in the formation of more than one recombination product. At least one recombination product contains said DNA sequence of interest. Other recombination products may be formed that do not contain said DNA sequence of interest.

Said DNA sequence of interest contains sequence portions from at least two of said at least two different vectors. At least two of said sequence portions are necessary for expressing said function of interest from said DNA sequence of interest. Therefore, said function of interest cannot be expressed, if only one vector is provided to said plant cells or said plant. Said DNA sequence of interest may of course also contain sequences deriving from said at least two different vectors that are not necessary for expressing said function of interest.

In a basic embodiment, said plant or said plant cells are provided with two different vectors and a recombination product containing said DNA sequence of interest is assembled from these two different vectors. Said DNA sequence of interest will then contain the two sequence portions of these two different vectors. In a more complex embodiment, said plant or said plant cells are provided with three or more different vectors, which allows the assembly of two or more recombination products each containing a different DNA sequences of interest. Each of said two or more different DNA sequences of interest is preferably assembled from two different vectors. This allows the production of two or more different transgenic plants or plant cells, each transformed on a chromosome with a different DNA sequence of interest. As an example, said plant or plant cell may be provided with three different (types of) vectors referred to as vector A, vector B, and vector C, said vectors containing sequence portions a, b, and c, respectively. Site-specific recombination between vector A and vector B allows assembly of DNA sequence of interest ab. Site-specific recombination of vector A and vector C allows assembly of DNA sequence of interest as. Thus, after segregation and/or selection, two different transgenic plants may be obtained, one being transformed on a chromosome with DNA sequence of interest ab and the other one being transformed on a chromosome with DNA sequence of interest ac. Depending on the arrangement of recombination sites on these three vectors, further DNA sequences of interest may be assembled (e.g. DNA sequences of interest bc, ba, ca, or cb) and further transgenic plants or plant cells may be produced accordingly, each being transformed on a chromosome with one of these DNA sequences of interest.

By providing plant cells or plants with many different vectors, a large number of different DNA sequences of interest (e.g. dozens, hundreds or even more different DNA sequences of interest) may be assembled and introduced into a chromosome for producing many different transgenic plants or plant cells. DNA libraries may in this way be provided to plants or plant cells. The transgenic plants or plant cells produced thereby may then be screened for a useful trait or a desired phenotype. It is in such screening methods where the full potential of the present invention can be made use of.

If three or more different types of vectors are used in the process of the invention, each vector may be adapted to recombine with all other of said at least two different vectors. In the above example with vectors A, B, and C, up to six different DNA sequences of interest may then be formed (ab, ac, bc, ba, ca, and cb). In this general embodiment, the largest combinatorial variety of DNA sequences of interest (and thus transgenic plants) may be formed. In a more special embodiment, a primary vector may be used in a mixture with a set of secondary vectors. Different DNA sequences of interest may then be formed, each containing a sequence portion from said primary vector and a sequence portion from a vector of said set of secondary vectors. The primary vector may e.g. provide sequences that render sequence portions of the secondary vectors expressible after assembly of a DNA sequence of interest containing a sequence portion of said primary vector and a sequence portion of a vector of said set of secondary vectors.

For producing transgenic plants or plant cells that are transformed on a chromosome with a DNA sequence of interest, said at least two different vectors are adapted for integrating said DNA sequence of interest into said chromosome. Said chromosome may be a nuclear chromosome, a plastid chromosome, or a mitochondrial chromosome. Nuclear and plastid chromosomes are preferred and a nuclear chromosome is most preferred. Said adaption for integration depends on the type of chromosome. For integrating said DNA sequence of interest in the plastid chromosome, i.e. the plastome, homologous recombination may e.g. be used. In this case, said vectors and/or the respective sequence portions are adapted such that the recombination product that contains said DNA sequence of interest also contains sequences homologous to plastome sequences for allowing integration of said DNA sequence of interest in the plastome. The sequences homologous to plastome sequences are preferably chosen such that integration takes place at a desired site of the plastome. Methods of plastome transformation are well-established for several plant species, see e.g. Svab et al., 1990 Proc Natl Acad Sci USA. 87, 8526-8530; Koop et al., 1996, *Planta,* 199, 193-201; Ruf et al., Nat Biotechnol. 2001, 19 (9):870-875; for a review see Maliga, P. 2002, *Curr Opin Plant Biol.,* 5, 164-172; WO 02/057466.

Integration of a DNA sequence of interest into a nuclear chromosome may be achieved e.g. by site-targeted transformation into a pre-engineered integration site using site-specific recombination. Alternatively, said at least two different vectors are adapted such that said DNA sequence of interest or said non-replicating recombination product contains homology sequences that facilitate integration of said DNA sequence of interest into said chromosome by homologous recombination. Preferably, however, nuclear integration is achieved using Agrobacterial T-DNA left and right border sequences in said DNA sequence of interest (see further below and examples). For this purpose, said at least two different vectors are adapted such that said DNA sequence of interest in said non-replicating recombination product has T-DNA border sequences. One or all of said at least two different vectors may contain a functional cytokinin autonomy gene, whereas said DNA sequence of interest is preferably devoid of a functional cytokinin autonomy gene.

A transgenic plant or plant cells transformed on a chromosome with a DNA sequence of interest is capable of expressing a function of interest from said DNA sequence of interest Produced transgenic plants or plant cells that are not capable of expressing a function or that express a function that is not of Interest, may be eliminated in step (b) of the process of the invention. Regarding said function of interest, the process of the invention is not limited. Typically, said function of interest is encoded in a coding sequence contained in said DNA sequence of interest. Said function of interest may be a function of DNA, RNA (notably messenger RNA) or of a protein encoded in said DNA sequence of interest. Preferably, said function of interest is a function of RNA or of a protein encoded in said DNA sequence of interest and expression of said function requires transcription of a coding sequence in said DNA sequence of interest. If said function is a function of a protein encoded in said DNA sequence of interest, expression of said function requires transcription and translation of a coding sequence of said DNA sequence of interest. For said transcription and optionally said translation, the DNA sequence of interest should contain the control elements needed therefore, like a pomoter, a 5'-non-translated region, a 3'-non-translated region, and/or a polyadenylation signal, etc. Said function of interest may e.g. be an antibiotic resistance that may be used for said selection of step (b). More than one function of interest may be expressed from said DNA sequence of interest. Said function of interest is normally related to the reason for performing the process of the invention. Typically, a selectable marker used in step (b) of the invention is among the functions of interest that can be expressed from said DNA sequence of interest.

At least two sequence portions of at least two different vectors are necessary for expressing said function of interest from said DNA sequence of interest. Said function of interest is rendered expressible by assembling said DNA sequence of interest by site-directed recombination between at least two of said at least two different vectors. There are several possibilities how said function of interest can be rendered expressible according to the invention:

Said assembling of said DNA sequence of interest may e.g. bring a coding sequence encoding said function of interest under the control of a regulatory element (e.g. a promoter) necessary for expressing said coding sequence. Thus, a functional expression unit may be formed in said DNA sequence of interest by said assembly. This possibility is particularly preferred if the process of the invention is used for screening a large number of DNA sequences like a collection of DNA sequences (e.g. a library) for a useful trait. Said collection of DNA sequences may e.g. be differently mutated forms of a chosen coding sequence of a protein, whereby said differently mutated forms may e.g. be produced by randomly introducing mutations (e.g. by error-prone PCR or gene shuffling), and a mutant protein encoded by said chosen coding sequence having desired properties may be identified with the process of the invention. In such a screening process, a primary vector may provide said regulatory sequence(s) required for expressing a test sequence from said library and a set of secondary vectors each contains a different test sequence. In this way, a set of transgenic plant cells or plants may be produced each containing a different DNA sequence of interest, whereby these different plants or plant cells may be screened for a useful function of interest (a useful trait of interest) encoded in one of said test sequences.

Alternatively, the process of shuffling can be performed in planta during the process of site-specific recombination-mediated assembly of said DNA sequence of interest. As is shown in FIG. 1B, the vector families $A_n$ and $B_n$ may be libraries of different variants of structural/functional domains of a protein of interest. Joining said domains through site-specific recombination can create combinatorial diversity of the protein of interest generated in planta. The coding sequences of the diversified protein of interest are stably integrated into plant chromosomal DNA. A schematic representation of a vector most suitable for such shuffling is shown in FIG. 11.

Another important embodiment allows screening for optimal regulatory sequences (e.g. a promoter) for optimally (in whichever sense) expressing a chosen coding sequence. In this case, a primary vector may provide said coding sequence and a set of different regulatory sequences are provided with a set of secondary vectors. Various transgenic plants or plant cells containing various DNA sequences of interest may be screened and a suitable regulatory element for expressing said chosen coding sequence may be found.

In a further embodiment, said assembling of said DNA sequence of interest may bring together fragments of a coding sequence that codes for a function of interest to be expressed. Preferably, two fragments of a coding sequence are brought together by said assembling, whereby each fragment is provided with a different sequence portion of a different vector. Preferably, each fragment of said coding sequence is not capable of expressing said function of interest in the absence of the other fragment. This may be easily achieved by splitting a coding sequence into two fragments such that each fragment contains a portion necessary for expressing the function of interest. Said two fragment may then be introduced in a vector, whereby two different vectors according to this invention are formed. Each sequence portion may provide some of the regulatory sequences required for expressing said coding sequence from said assembled DNA sequence of interest.

For rendering said coding sequence expressible, expression of said function of interest from said DNA sequence of interest may comprise intron-mediated cis-splicing. Said assembling may assemble concomitantly an intron, notably a self-splicing intron, such that splicing of an RNA expression product of said coding sequence results in an mRNA having both fragments properly connected to each other such that a desired protein may be correctly translated (e.g. as depicted in FIGS. 10 and 11). In more detail, a first vector of said at least two different vectors may contain
  a first sequence portion that contains: a first part of a sequence coding for the function to be expressed and, downstream thereof, a 5' part of an intron, and
a second vector of said at least two different vectors may contain a second sequence portion that contains: a second part of a sequence coding for a function to be expressed and, upstream thereof, a 3' part of an intron.

This important embodiment is also illustrated in the examples.

In step (b) of the process of the invention, transgenic plants or plant cells expressing said function of interest are selected. Said selecting may comprise applying an antibiotic or inhibitor suitable for said selectable marker to plant cells or plants obtained in step (a). Said selecting may also comprise screening for transformed plants or plant cells in which recombination between at least two of said at least two different vectors has occurred. Further, said selecting preferably comprises selection for integration of said DNA sequence of interest into said chromosome. Step (b) may also comprise allowing segregation of differently transformed plant cells, notably of plant cells containing different (e.g. differently assembled) DNA sequences of interest. Said selecting, and optionally said segregating, may comprise the use of a selectable marker gene e.g. on said DNA sequence of interest. For this purpose, said at least two different vectors may be adapted such that said DNA sequence of interest contains a selectable marker gene or another sequence that allows screening for transformed plants or plant cells containing said DNA sequence of interest.

Step (b) may be implemented by many different embodiments. A sequence portion of one of said at least two different vectors may contain a selectable marker, whereby said selectable marker is included in said DNA. sequence of interest by said assembling. In a strongly preferred embodiment, said selectable marker is turned on by said assembling of said DNA sequence of interest such that it provides an antibiotic resistance to plant cells containing said assembled DNA sequence of interest but it does not provide antibiotic resistance to cells in which said assembling has not occurred. Most preferably, the selectable marker gene cannot be transcribed in said plant cells from one of said at least two different vectors. This embodiment may be implemented such that said selectable marker is placed under the control of a genetic element, allowing transcription of said selectable marker gene after said assembling of said DNA sequence of interest, e.g. by placing the coding sequence of said selectable marker under the control of a promoter. Advantageously, an IRES (internal ribosome entry site) element may control translation of said selectable marker (cf. FIG. 11). References describing the use of IRES elements are given below.

In a further important embodiment, said transgenic plants or plant cells are screened for the absence of one or all of said at least two different vectors and/or for the absence of recombination products thereof with the exception of recombination products containing said DNA sequence of interest. With this embodiment, the production of transgenic plants or plant cells can be avoided that contain unnecessary foreign DNA sequences deriving from said at least two different vectors. These unnecessary foreign DNA sequences may disturb expression of said DNA sequence of interest or may compromise the determination of said function of interest (e.g. in functional genomics studies). This embodiment may be implemented with the use of a counter-selectable marker. Optionally, said screening may be supported by PCR analysis and selection of suitable transformants. At least one of said at least two different vectors may contain a counter-selectable marker gene or another sequence that allows efficient screening against transformed cells containing one of said at least two different vectors. Preferably, said at least two different vectors are adapted such that, after said recombination, said counter-selectable marker gene is contained in recombination products other than nucleic acid molecules containing said DNA sequence of interest. Said counter-selectable marker gene or said another sequence that allows efficient screening against transformed cells containing one or more of said at least two different vectors may advantageously be under translational control of an internal ribosome entry site (IRES) element.

The invention also provides transgenic plants or parts thereof like seeds produced by the process the invention. Preferably, all coding sequences and/or expressible sequences of said sequence of interest in said transgenic plants or parts thereof are of plant origin. Moreover, library of plants, of plant cells, or of plant seeds obtained or obtainable according to process of the invention are provided.

PREFERRED EMBODIMENTS OF THE INVENTION

A process of producing transgenic multi-cellular plants or plant cells stably transformed on a nuclear chromosome with a DNA sequence of interest and capable of expressing a function of interest from said DNA sequence of interest, said process comprising:
(a) providing plant cells or plants with at least two different vectors by *Agrobacterium*-mediated delivery, whereby
  (i) said at least two different vectors are adapted to recombine with each other by site-specific recombination in said plant cells for producing a non-replicating recombination product containing said DNA sequence of interest,
  (ii) said at least two different vectors are adapted for integrating said DNA sequence of interest into said chromosome such that said DNA sequence of interest contains T-DNA border sequences,
  (iii) said DNA sequence of interest contains sequence portions from at least two of said at least two different vectors, said sequence portions being necessary for expressing said function of interest from said DNA sequence of interest; and
(b) selecting plants or plant cells expressing said function of interest.

A process of producing different transgenic multi-cellular plants or plant cells transformed on a chromosome, preferably a nuclear chromosome, with a DNA sequence of interest and capable of expressing a function of interest from said DNA sequence of interest, said process comprising the following steps (A) and (B):
(A) providing plants or plant cells with a mixture of
  (i) a primary vector having a primary sequence portion $a_1$ and
  (ii) a set of n secondary vectors each having a secondary sequence portion selected from the set $(b_1, b_2, \ldots, b_n)$, whereby
  n is an integer of >1,
  said primary sequence portion $a_1$ is necessary for expressing the function of a secondary sequence portion $(b_1, b_2, \ldots, b_n)$,
  said primary vector and said secondary vectors are adapted such that said primary vector can recombine with every member of said set of n secondary vectors by site-specific recombination for producing recombination products containing different DNA sequences of interest of the type $(a_1b_1, a_1b_2, \ldots, a_1b_n)$ or the type $(b_1a_1, b_2a_1, \ldots, b_na_1)$, said primary vector and said secondary vectors are adapted to integrate said DNA sequences of type $(a_1b_1, a_1b_2, \ldots, a_1b_n)$ or type $(b_1a_1, b_2a_1, \ldots, b_na_1)$ into a chromosome,
(B) selecting transformed plants or plant cells expressing a function of interest, preferably from a DNA sequence of interest of type $(a_1b_1, a_1b_2, \ldots, a_1b_n)$ or type $(b_1a_1, b_2a_1, \ldots, b_na_1)$.

Said different transgenic multi-cellular plants differ inter alia in that they contain different DNA sequences of interest Said recombination products containing a DNA sequences of interest may be replicating or non-replicating. Preferably, they are non-replicating as defined in the general description of the invention. Said mixture of primary and secondary vectors is preferably provided to said plant cells by a mixture of *Agrobacterium* cells, each cell providing one type of vector.

I—assembly of a DNA sequence of interest (AB) from two different vectors (A and B) by site-specific recombination.

II—assembly of a DNA sequence of interest (AB) from two precursor vectors (AA' and B'B) that include helper sequences (A' and B') absent in said DNA sequence of interest (AB).

Figure 1A:
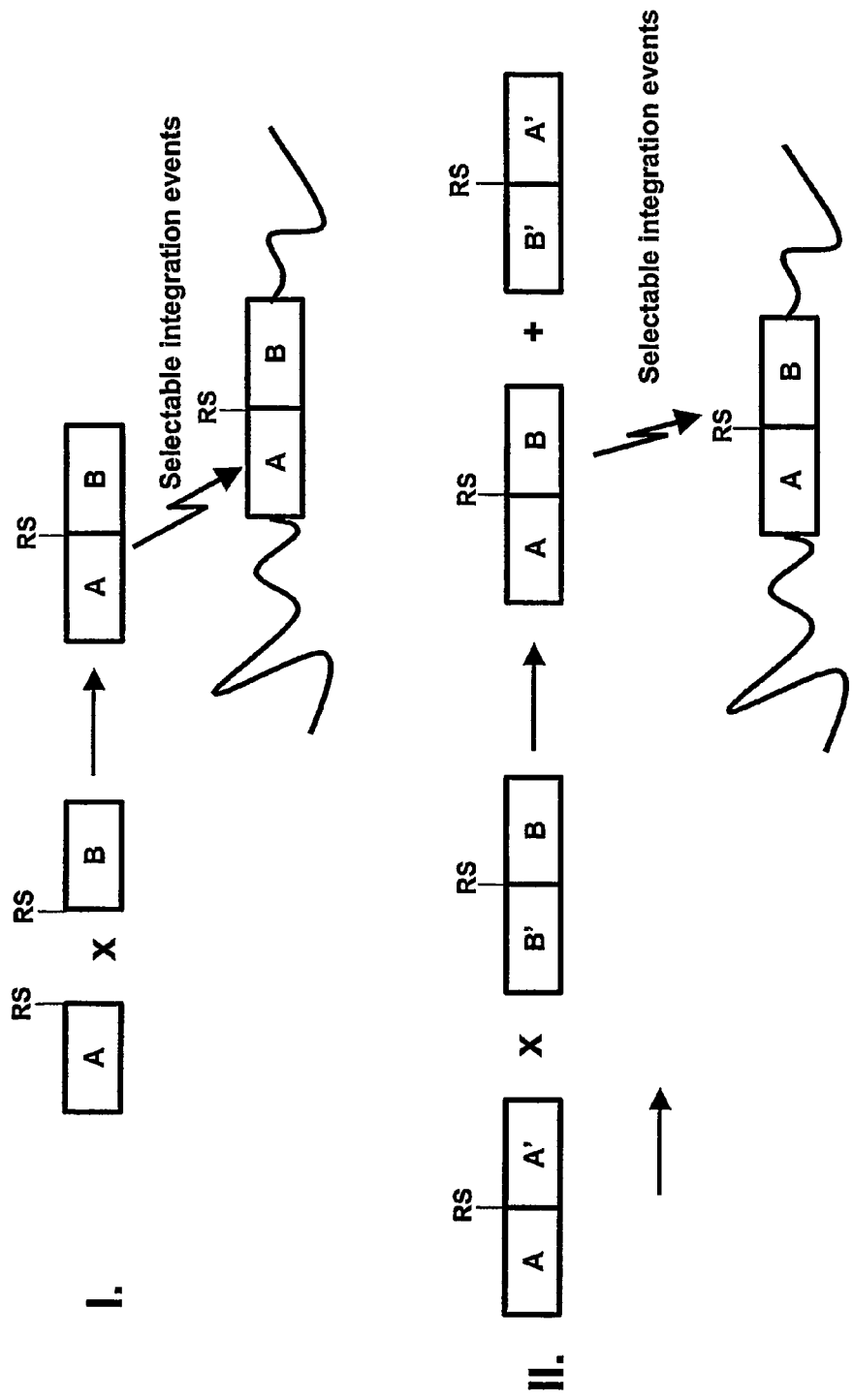
FIG. 1A shows schematically the assembly of a DNA sequence of interest from two (precursor) vectors.
Figure 1B:
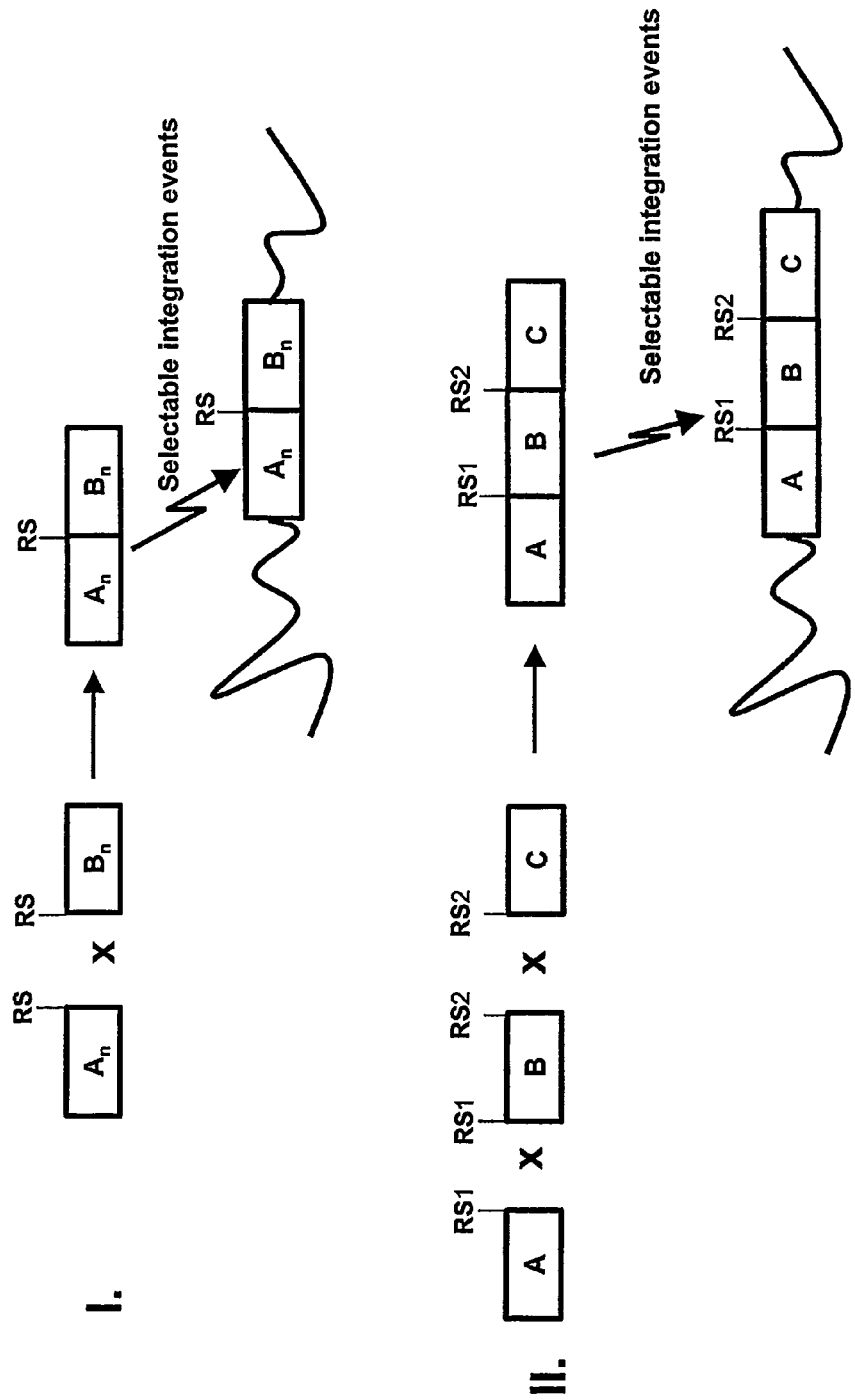
FIG. 1 shows the general scheme of in planta assembly of a DNA sequence of interest designed for stable integration into plant chromosomal DNA. RS stands for recombination sites.

FIG. 1B—shows schematically the assembly of a DNA sequence of interest from more than two different vectors.

I—assembly of a DNA sequence of interest having two-components $(A_nB_n)$ from a library of the precursor vectors A and B, where n is the number of precursor vectors in the library.

II—assembly of the three component DNA sequence of interest (ABC) from a library of the precursor vectors A, B and C. $RS_1$ and $RS_2$ are recombination sites recognised by different recombinases/integrases.

Figure 2:
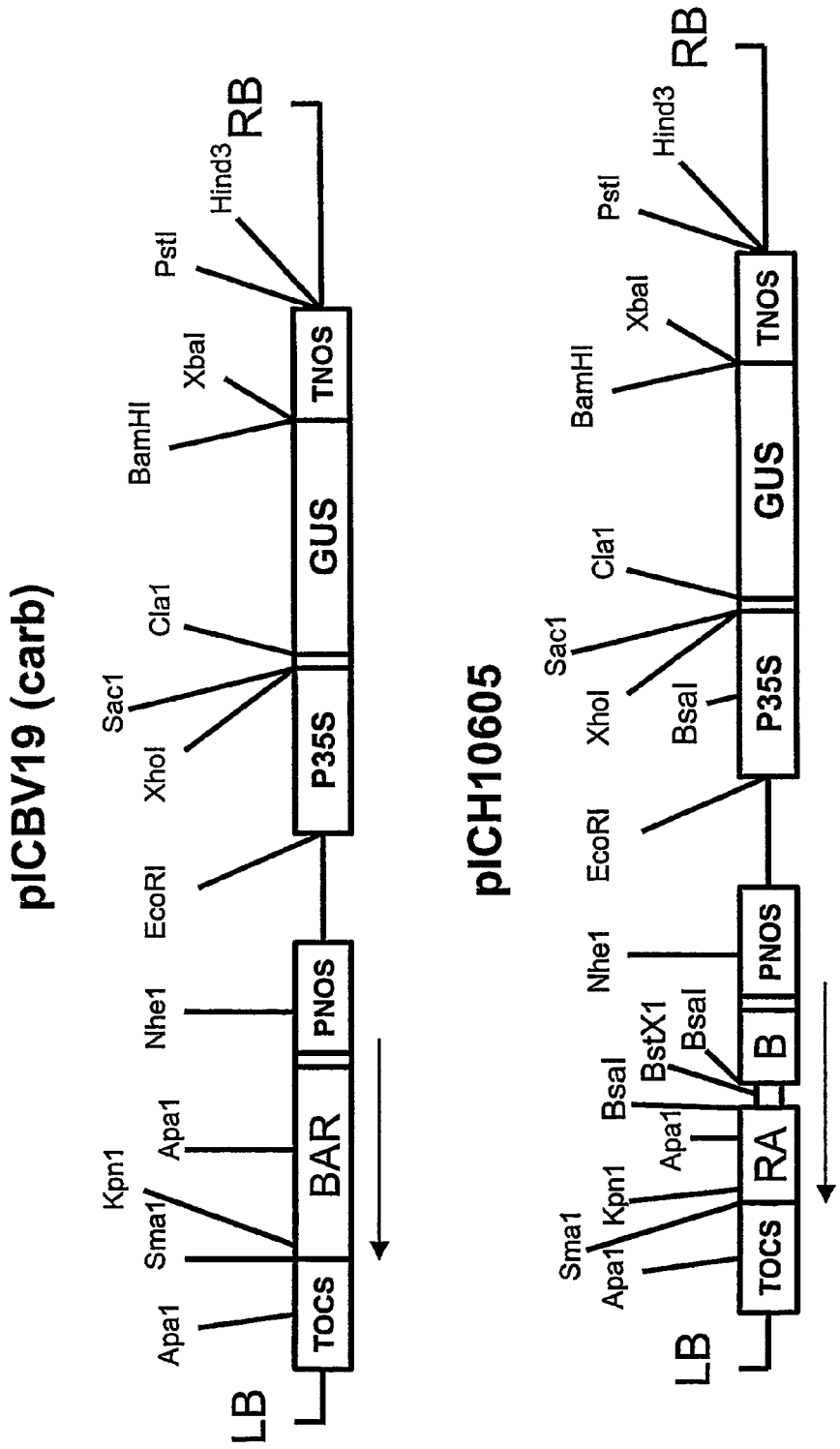

FIG. 2 depicts schematically the T-DNA regions of binary vectors pICBV19 and pICH10605. GUS—beta-glucuronidase gene; P35S—CaMV35S promoter; BAR—phosphinothricin acetyltransferase gene (pICH10605 has intron disrupting BAR coding sequences); PNOS—promoter of agrobacterial nopaline synthase gene; TNOS—transcription termination region of agrobacterial nopaline synthase gene; TOCS—transcription termination region of octopine synthase gene.

Figure 3:
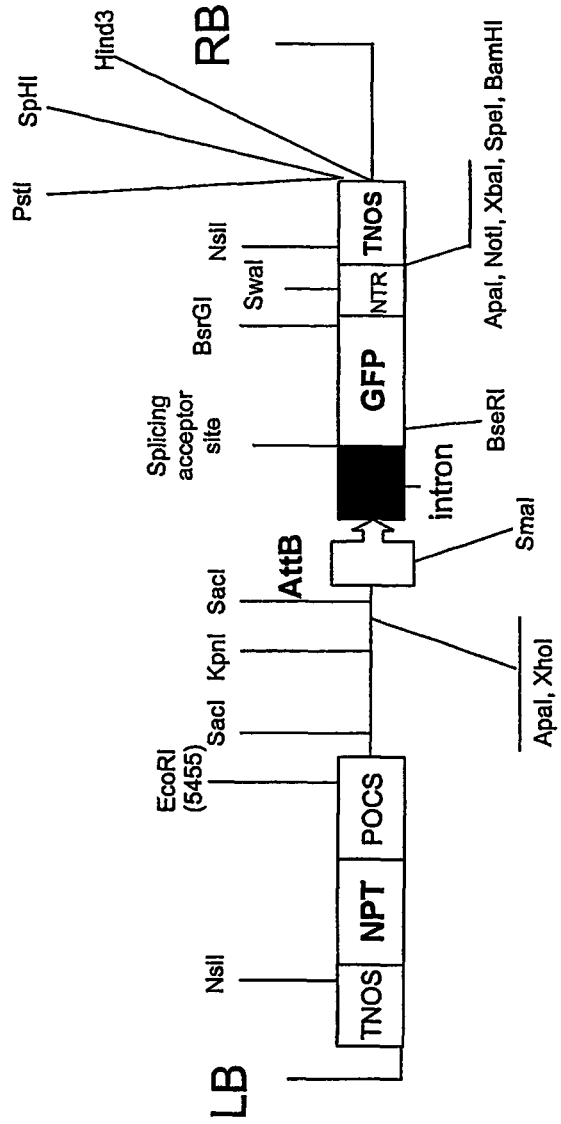

FIG. 3 depicts schematically the T-DNA region of binary vector pICH7410.

GFP—gene encoding green fluorescent protein; NPT—neomycin phoshotransferase II gene conferring resistance to kanamycin; POCS—promoter region of the agrobacterial octopine synthase gene; NTR—3' non-translated region of tobacco mosaic virus (TMV) RNA; AttB—recombination site.

Figure 4:
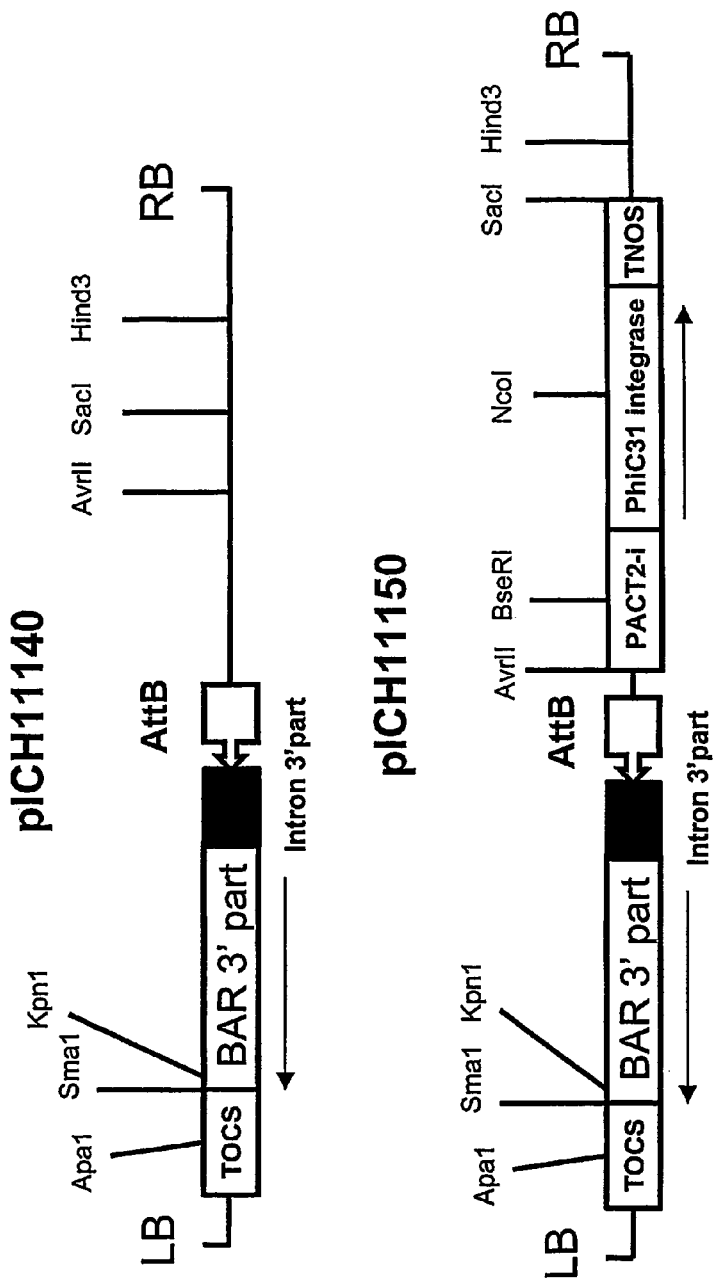

FIG. 4 depicts schematically the T-DNA regions of plasmids pICH11140 and pICH11150.

PACT2-i—promoter of the *Arabidopsis* actin2 gene with first intron.

Figure 5:
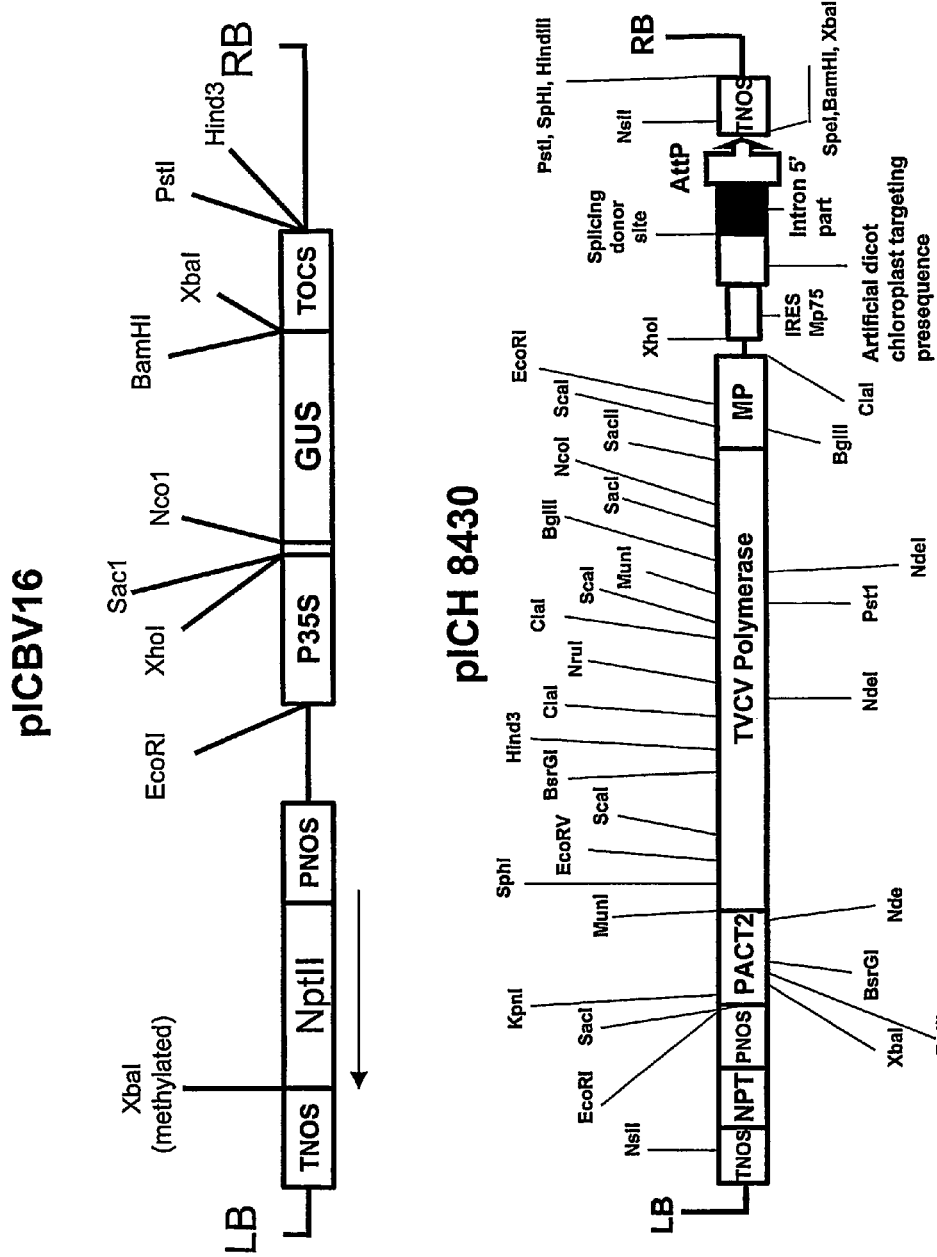

FIG. 5 depicts the T-DNA regions of the binary vectors pICBV16 and pICH8430.

PACT2—promoter of the *arabidopsis* actin2 gene; TVCV polymerase—RNA-dependent RNA polymerase of turnip vein-clearing virus (TVCV); MP—tobamoviral movement protein; IRESmp75—IRES of crTMV movement protein.

Figure 6:
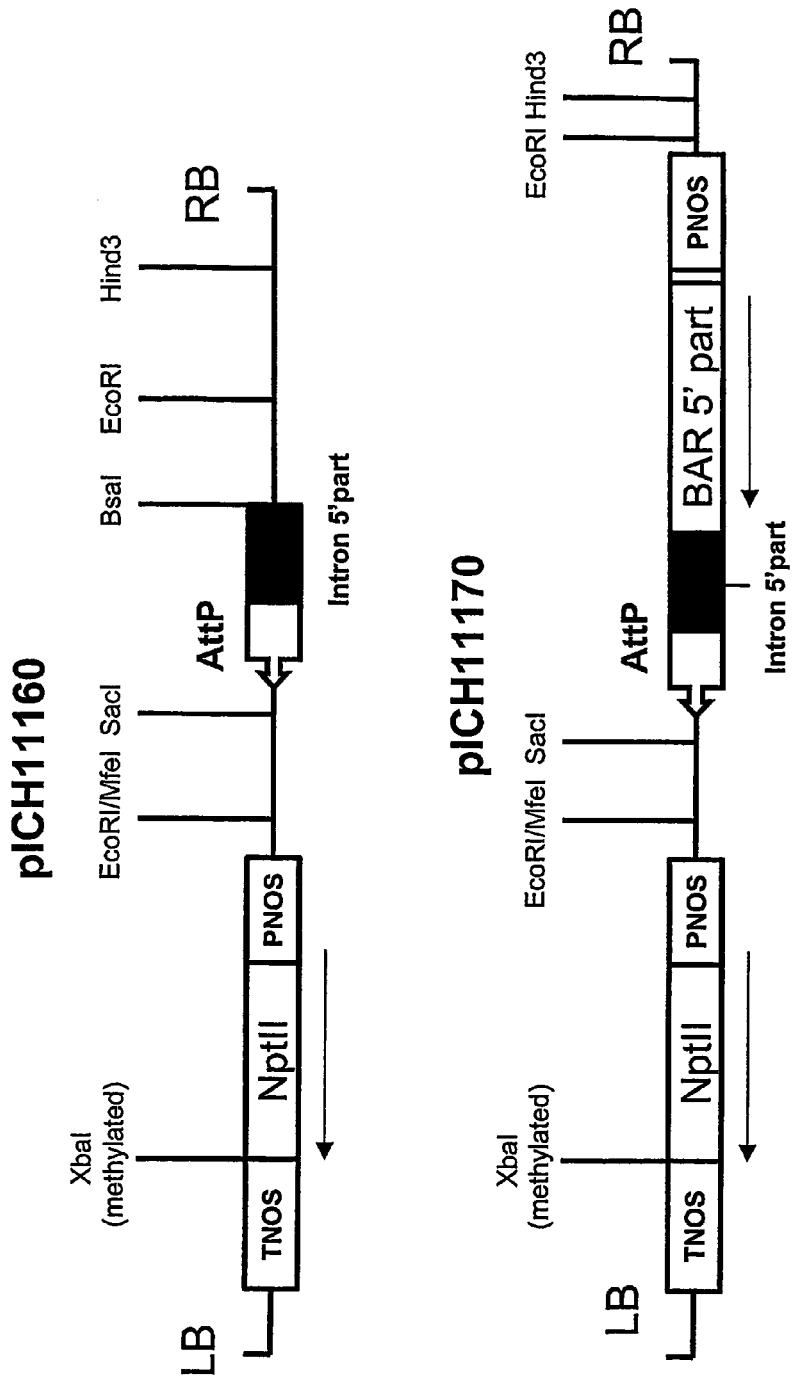

FIG. 6 depicts schematically the T-DNA regions of the binary vectors pICH11160 and pICH11170.

Figure 7:
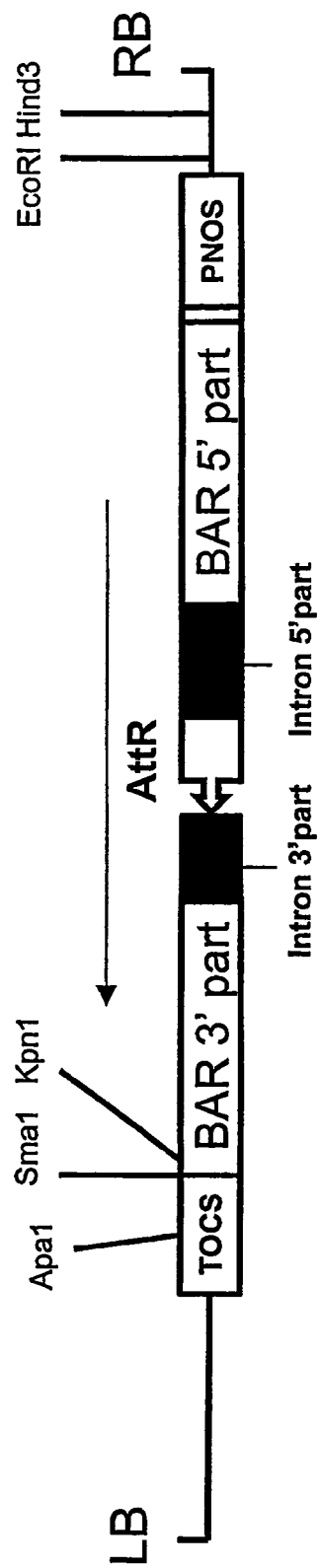

FIG. 7 depicts schematically the T-DNA region resulting from site-specific recombination between T-DNAs of pICH11150 and pICH11170. This region carries a BAR gene interrupted by an intron containing an AttR site. Intron splicing after transcription allows expression of a functional BAR protein.

Figure 8:
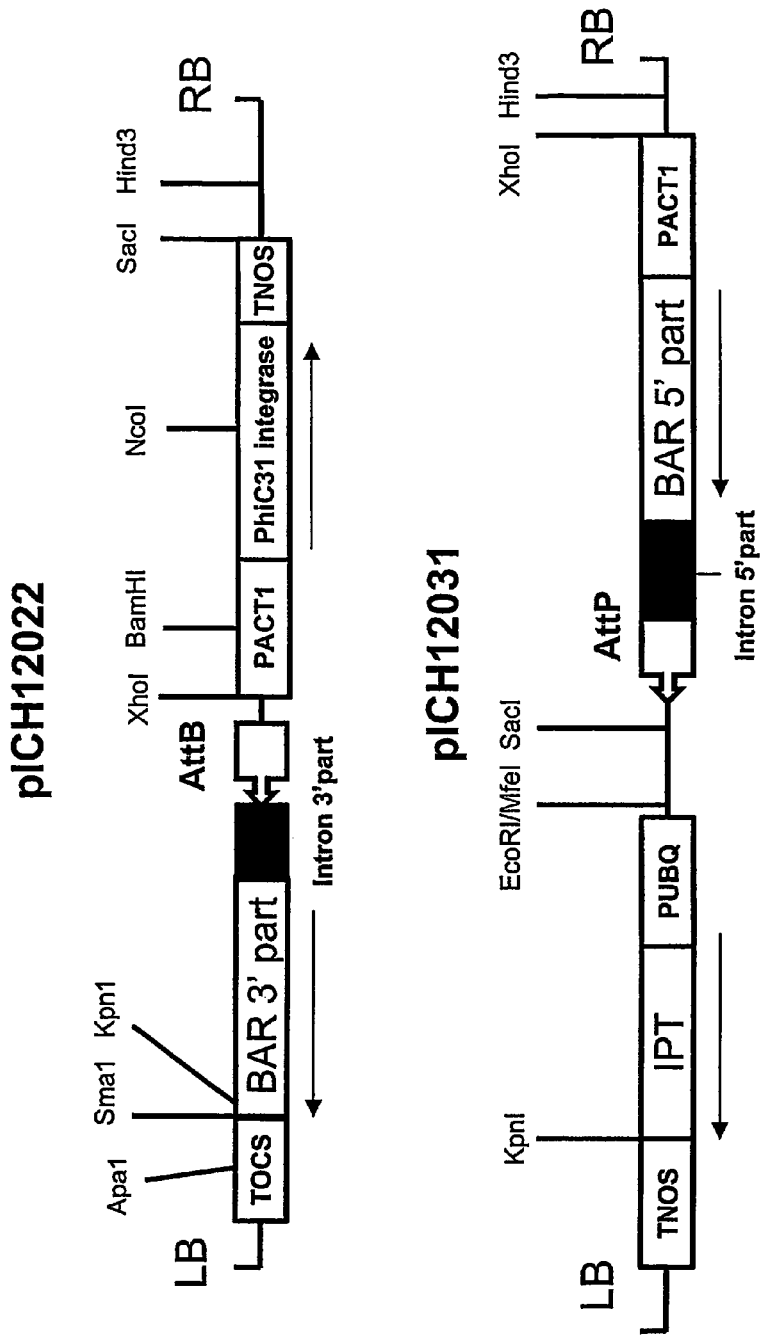

FIG. 8 depicts schematically the T-DNA regions of the binary vectors pICH12022 and pICH12031 designed for transformation of monocotyledonous plants. PUBQ—promoter of the maize ubiquitin gene; PACT1—promoter of the rice actin1 gene; IPT—gene coding for isopentenyl transferase.

Figure 9:
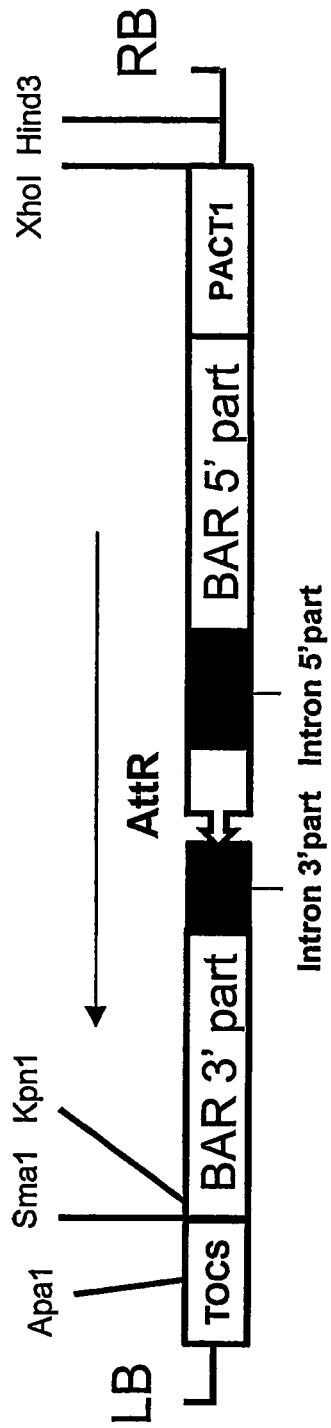

FIG. 9 depicts schematically the T-DNA region resulting from site-specific recombination between T-DNA regions of binary vectors pICH12022 and pICH12031. The region carries a functional BAR gene with an intron under control of the rice actin1 promoter PACT1.

Figure 10:
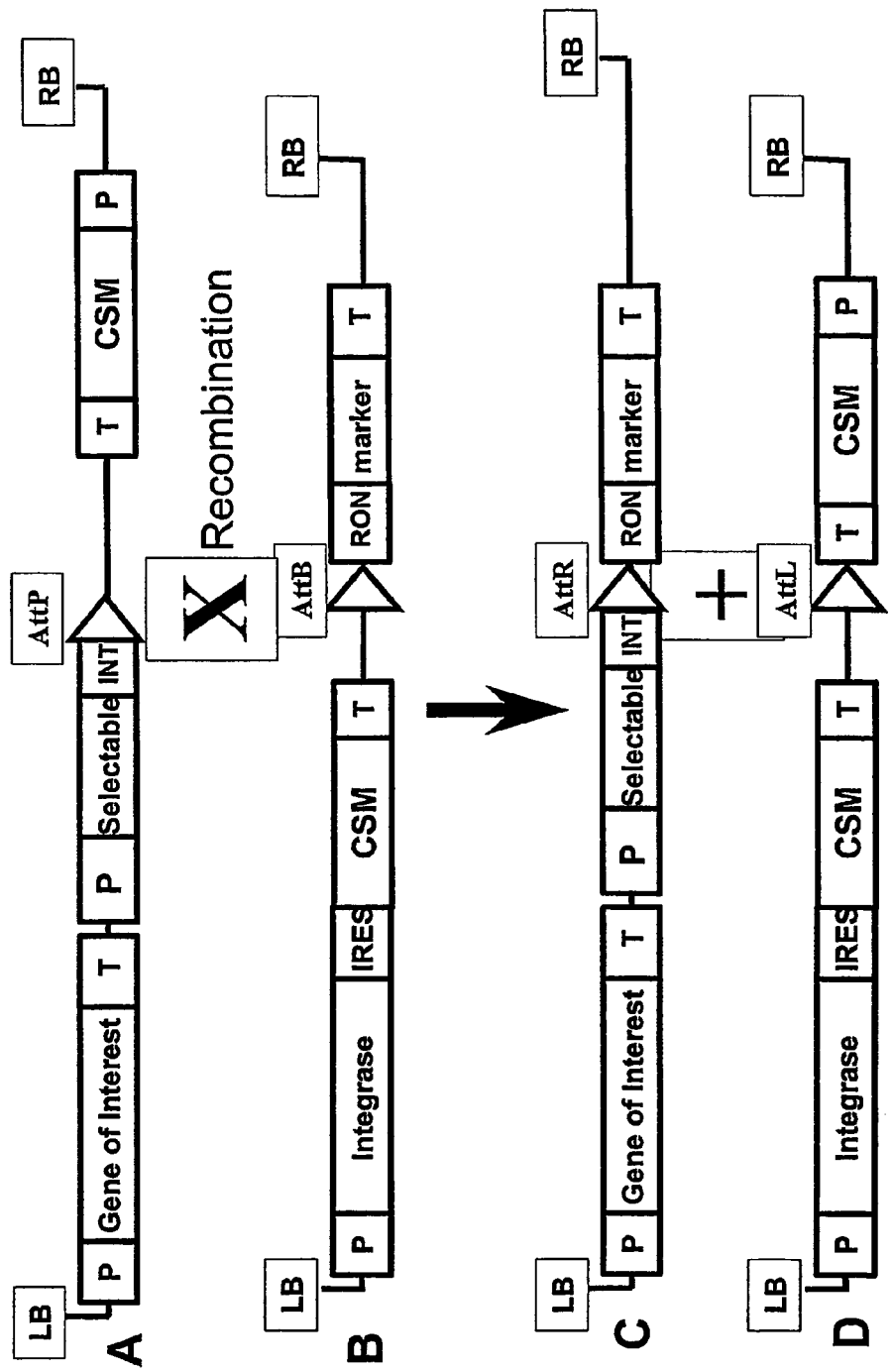

FIG. 10 depicts a scheme of assembling a DNA sequence of interest (C) from two precursor vectors (A and B) including assembly of a functional selectable marker gene from fragments of said selectable marker gene designated "Selectable" and "marker". Concomitantly, an intron (designated "INTRON") is assembled from intron fragments designated "INT" and "RON". P—promoter; T—transcription termination region; CSM—counter-selectable marker; IRES—internal ribosome entry site.

Figure 11:
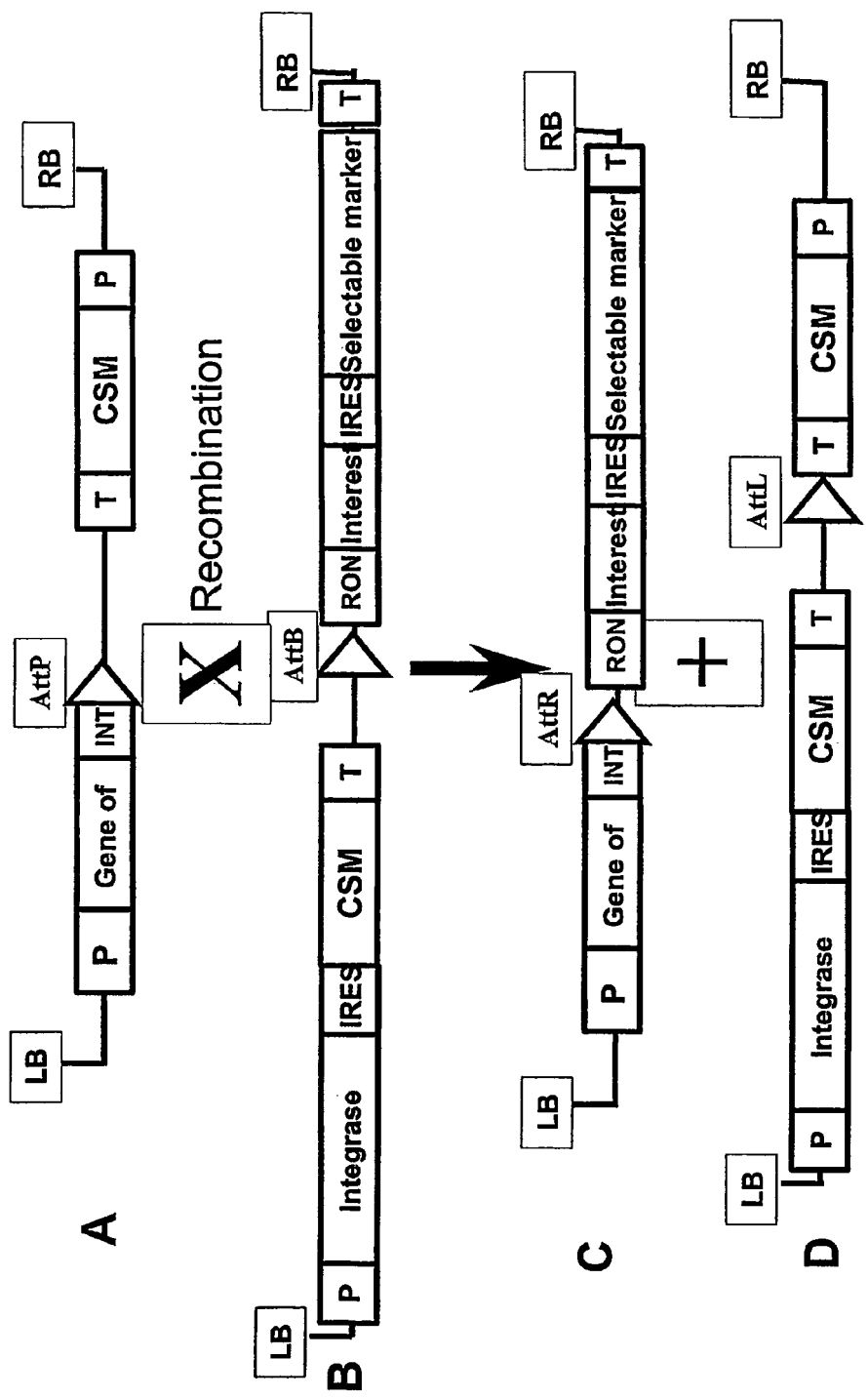

FIG. 11 depicts a scheme of assembling a DNA sequence of interest (C) from two precursor vectors (A and B) including assembly of a functional gene of Interest from fragments of said gene of interest designated "Gene of" and "Interest". A selectable marker under translational control of an IRES element is rendered expressible by said assembly by placing it under the transcriptional control of a promoter. Both precursor vectors A and B contain a counter-selectable marker gene CSM. By said assembling, CSM ends up in recombination product D that does not contain said gene of interest Using said CSM, transgenic plants or plant cells can be selected that do not contain precursor vector A, nor precursor vector B, nor recombination product D. P—promoter; T—transcription termination region; CSM—counter-selectable marker; IRES—internal ribosome entry site.

Figure 12:
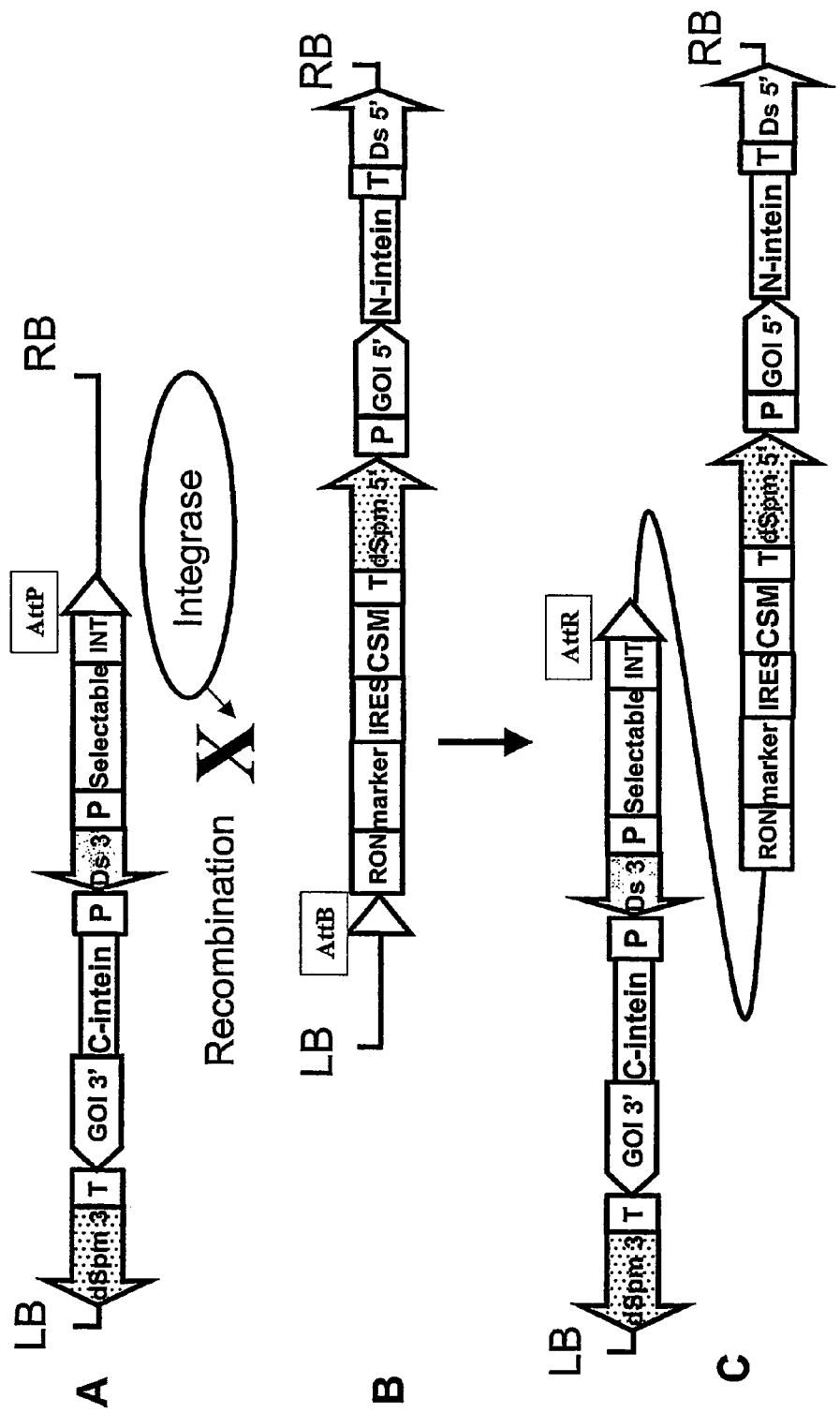

FIG. 12 depicts schematically assembly of a complex DNA sequence of interest C by site-specific recombination in planta of vectors A and B. P—promoter; T—transcription termination region; CSM—counter-selectable marker; IRES—internal ribosome entry site; Ds (3' or 5')—non-autonomous transposable element (Ds) ends recognised by the Ac transposase; dSpm (3' or 5')—non-autonomous transposable element (dSpm) ends recognised by Spm transposase; GOI—gene of interest.

Figure 13:
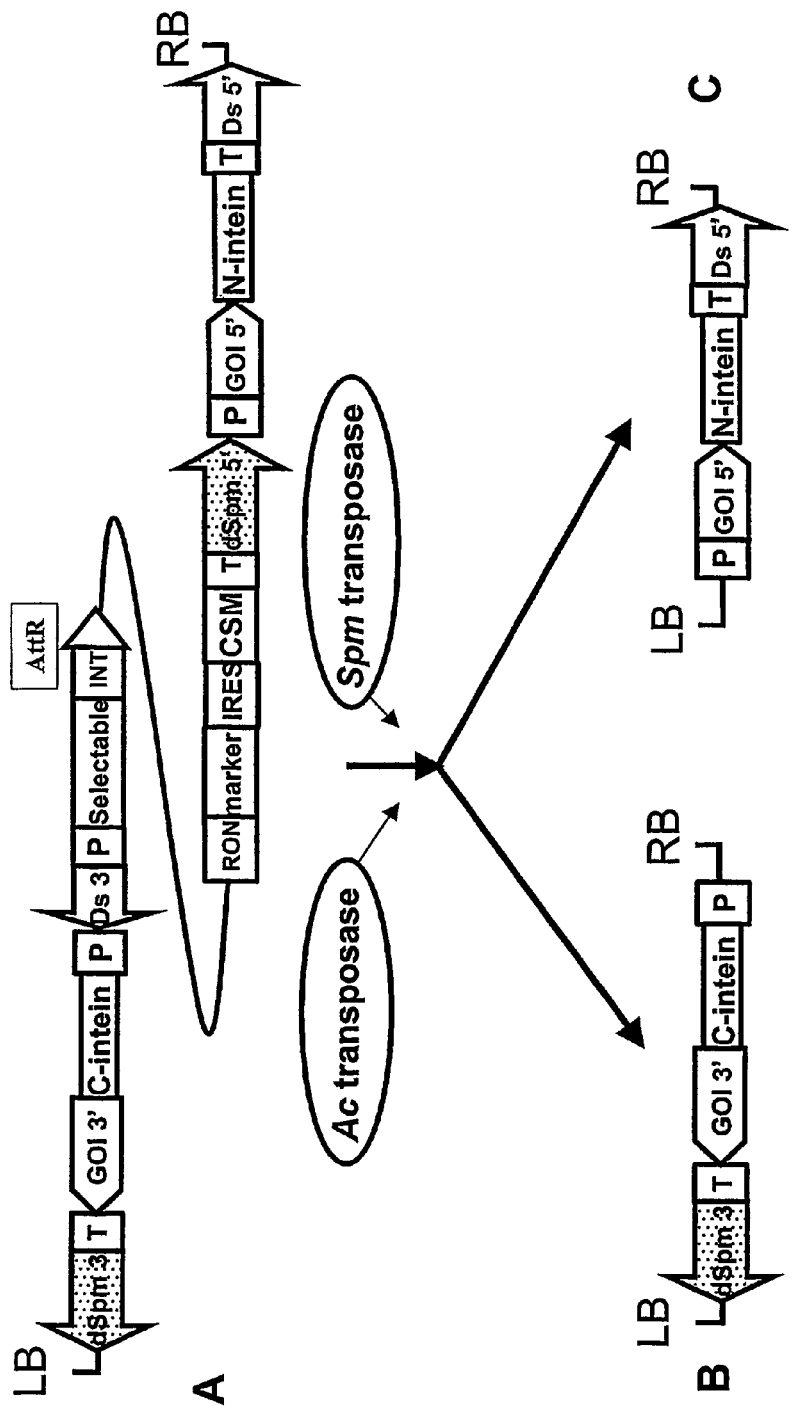

FIG. 13 depicts schematically a method of generating different allelic vectors from a DNA sequence of interest assembled in planta according to FIG. 12. P—promoter; T—transcription termination region; CSM—counter-selectable marker; IRES—internal ribosome entry site; Ds (3' or 5')—non-autonomous transposable element (Ds) ends recognised by Ac transposase; dSpm (3' or 5')—non-autonomous transposable element (dSpm) ends recognised by Spm transposase; GOI—gene of interest.

Figure 14:
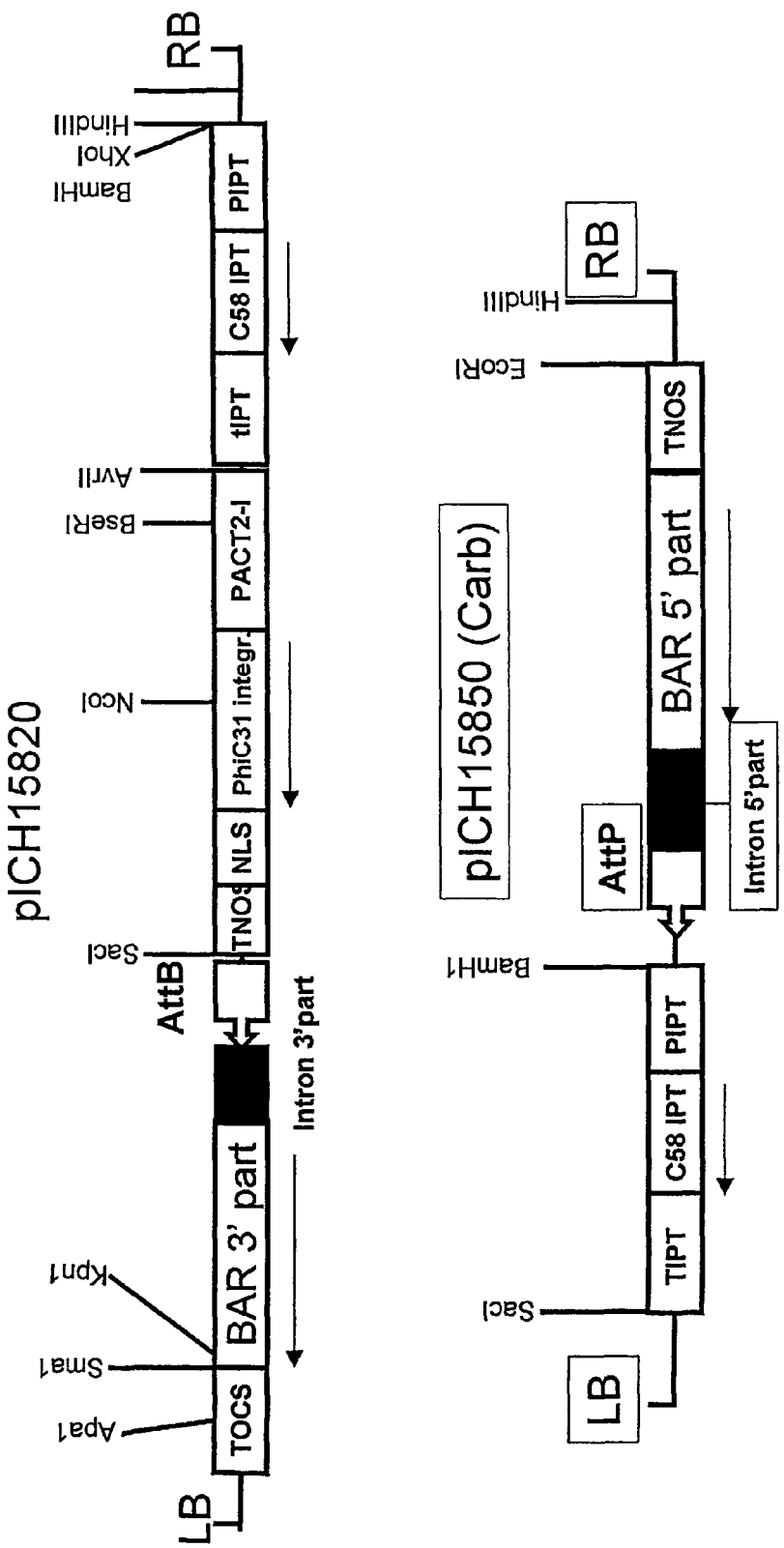

FIG. 14 depicts schematically the T-DNA regions of the binary vectors pICH15820 and pICH15850 designed for transformation of dicotyledonous plants. These vectors may be cotransformed into plants and complement each other according to the invention. PACT2-I—promoter of the Arabidopsis actin2 gene with intron; IPT—gene encoding for isopentenyl transferase; PIPT—IPT promoter; TIPT—IPT gene transcription termination region; NLS—nuclear localisation signal; TNOS—transcription termination region of agrobacterial nopaline synthase gene; TOCS—transcription termination region of octopine synthase gene.

Figure 15:
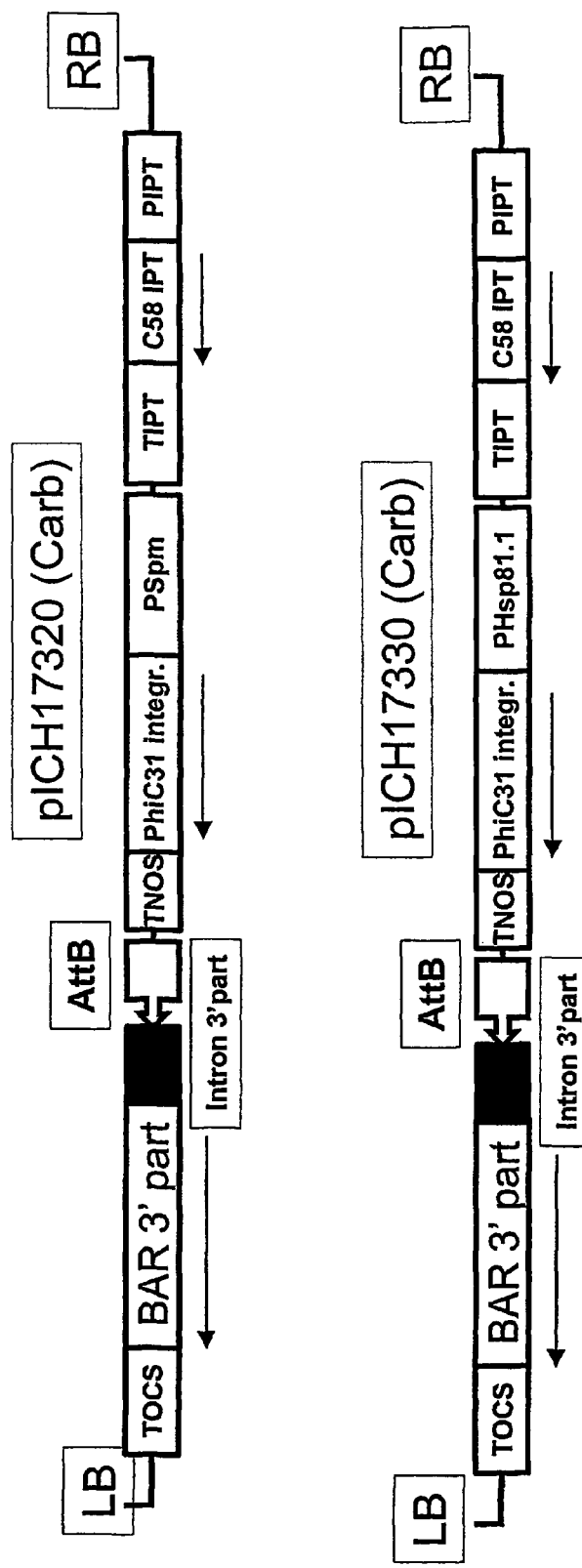

FIG. 15 depicts schematically the T-DNA regions of binary vectors pICH17320 and pICH17330 designed for transformation of dicotyledonous plants. These vectors may be cotransformed e.g. with pICH15850 for performing the process of the invention. PSpm—promoter of Z. mays Spm transposase; PHsp81.1—promoter of the Arabidopsis HSP81.1 gene; IPT—gene encoding isopentenyl transferase; PIPT—IPT promoter; TIPT—IPT gene transcription termination region; NLS—nuclear localisation signal; TNOS—transcription termination region of the agrobacterial nopaline synthase gene; TOCS—transcription termination region of octopine synthase gene.

Figure 16:
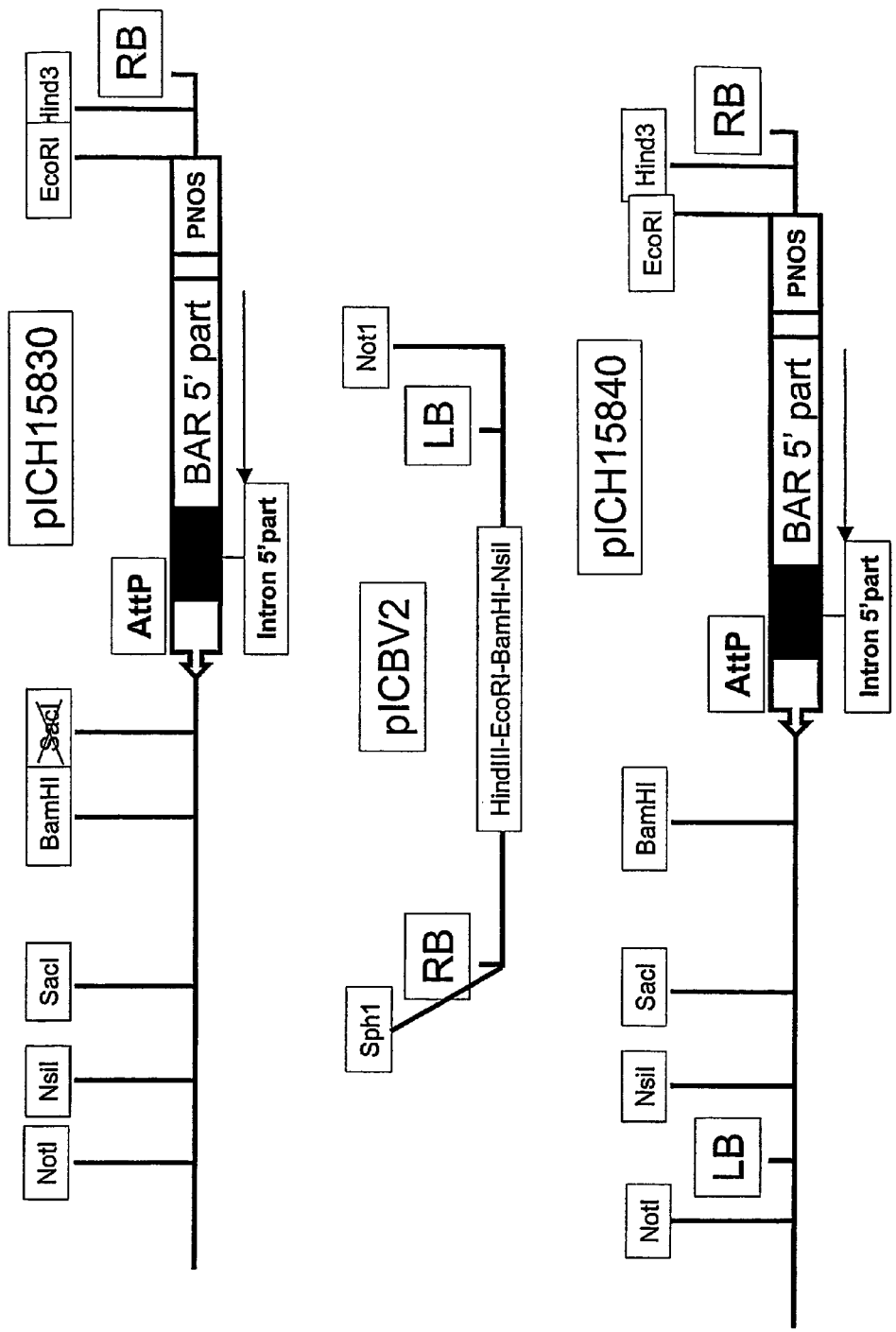

FIG. 16 depicts schematically vectors pICH15830, pICBV2, and pICH15840.

Figure 17:
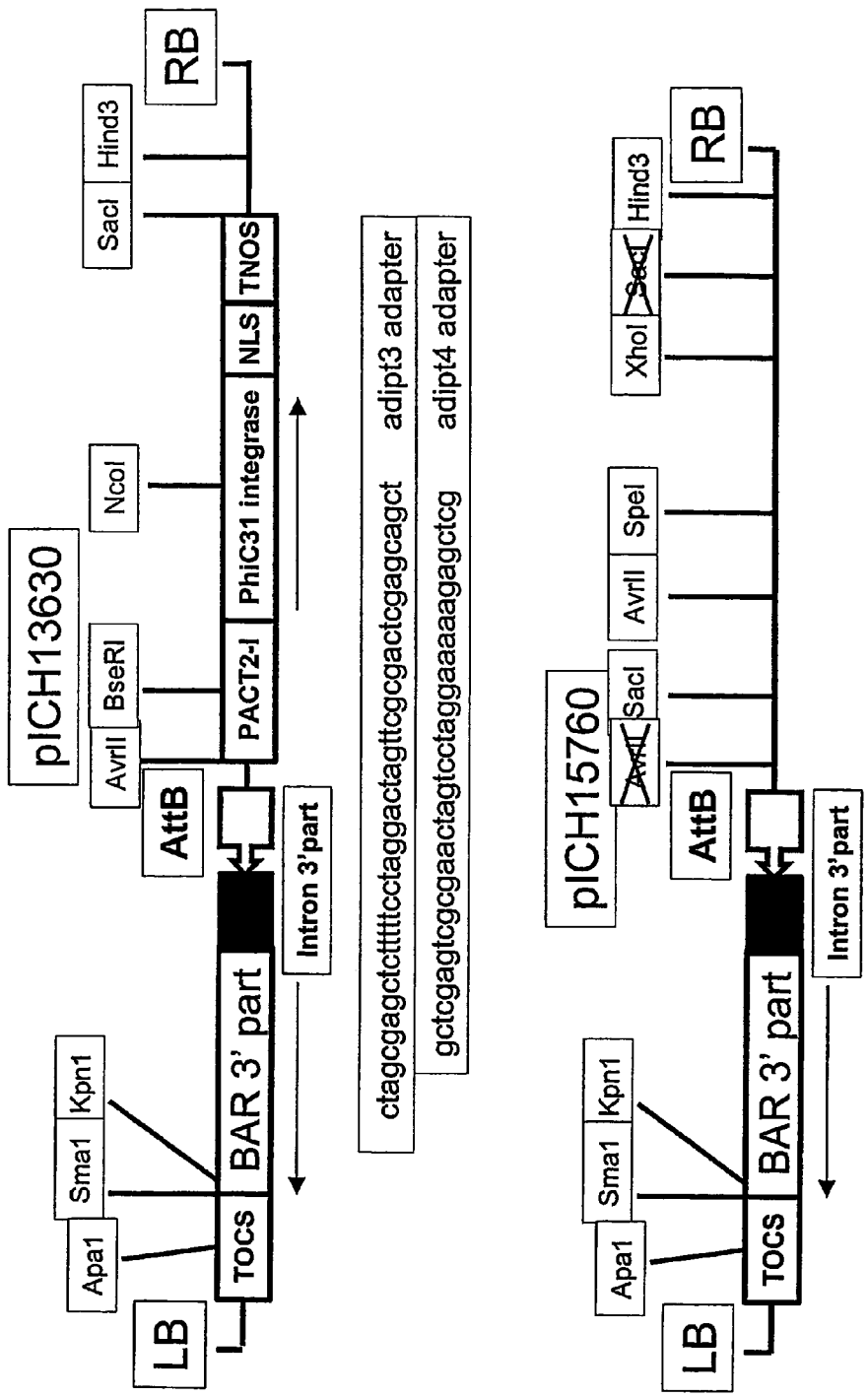
Figure 17:
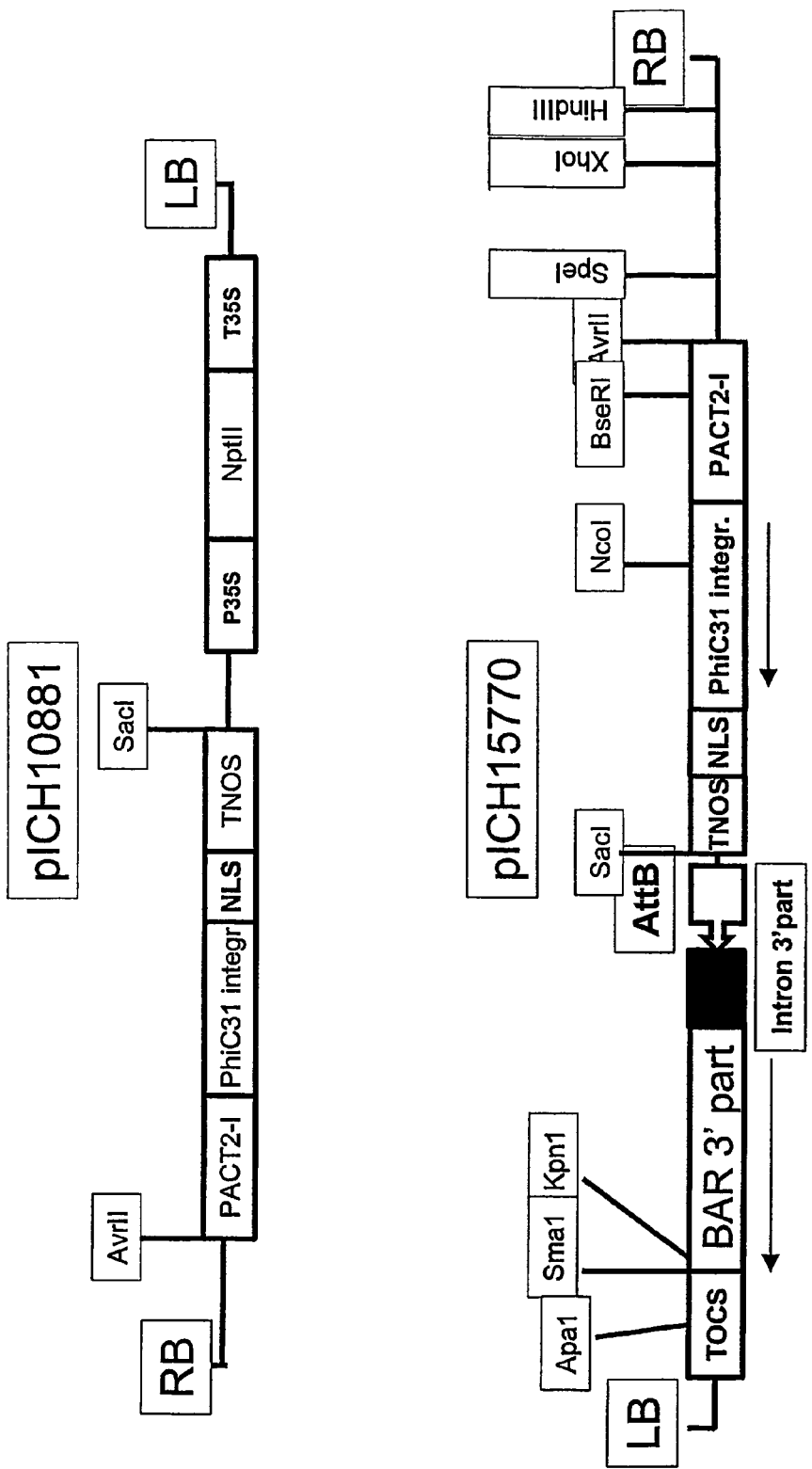

FIG. 17 depicts schematically vectors pICH13630, pICH15760 in (A), and pICH10881, pICH15770 in (B). The adipt3 and adipt4 adapters shown in (A) correspond to SEQ ID NOS: 7 and 8, respectively.

Figure 18:
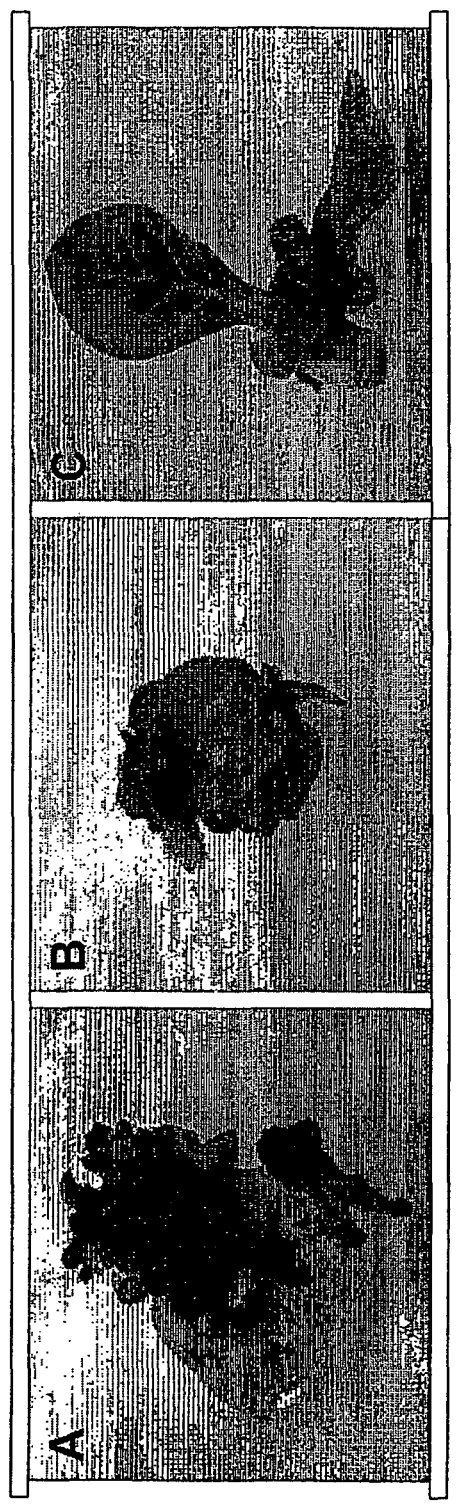

FIG. 18. Generation of tobacco transformants on nonselective hormone-free medium. Morphology of regenerated shoots containing T-DNA with an IPT gene (A, B) and without an IPT gene (C).

DETAILED DESCRIPTION OF THE INVENTION

In this invention we describe a process of rapid, inexpensive in planta assembly of a DNA sequence of interest designed for stable integration into a plant chromosome. This approach allows inter alia for fast optimization of the sequences to be expressed by testing various transcription, translation assembled units, units with different protein fusions or different protein targeting or post-translational modification, etc. It can be efficiently used for screening libraries of coding or regulatory sequences of interest. Another application of the invention is the design of safer vectors which are unable to transfer the sequence of interest through an illicit gene transfer. Also, difficult cloning can be avoided during the design of complex DNA regions (e.g. showing instability during cloning procedures in bacterial cells) for stable nuclear transformation, as two or more complex DNA fragments can be linked together in planta prior to integration into plant nuclear DNA.

Current methods of transient or constitutive transgene expression in plants usually employ introducing into plant cell assembled vector(s) with the gene(s) of interest. Transient expression of a sequence of interest is beyond the scope of this invention. The differences between transient and constitutive transgene expression are best exemplified, e.g. within the frame-work of plant functional genomics, where the use of viral vectors can relatively fast provide some initial information about a possible function of a transgene in some cases (WO993651; Kumagai et al., 1995, Proc. Natl. Acad. Sci. USA, 95, 1679-1683). In many other cases, no information or artefacts are obtained. Further, use of viral vectors does not allow further study of the function of a transgene, e.g. during plant development, etc. In addition, Agrobacteria or viral vectors as such cause severe changes in the plant cells, thus making it difficult to study, for example, the functions of genes involved in plant-pathogen interactions. Stably transformed transgenic plants with different expression patterns (e.g. inter- or intracellular compartmentalisation, tissue, organ or cell-specific expression) are required for detailed study of a gene of interest. According to the present invention, the assembly, optimization and identification of a desired DNA sequence of interest for stable nuclear transformation of plant cells can be performed with high efficiency in planta, thus be combined with plant transformation as a one step procedure. In the following, said at least two different vectors of the invention are also referred to as precursor vectors.

The general scheme of such assembly from two or more (precursor) vectors by site-specific DNA recombination is shown in FIG. 1. The simplest scheme of such assembly is the creation of a DNA sequence of interest ab from two precursors vectors A and B by recombination using the recombination site RS (FIG. 1A, I). Needless to say that such recombination event shall be selectable. This is easy to achieve e.g. if said recombination creates a functional gene providing for selection.

In one preferred embodiment of the invention, a T-DNA region (FIG. 7) including said DNA sequence of interest is assembled from two precursor vectors represented by two other T-DNA regions (FIGS. 4 and 6, bottom) through integrase PhiC31-mediated recombination. Said T-DNA region may contain a functional BAR gene that is absent in the precursor vectors, thus making possible the selection for said recombination event. The integrase necessary for assembly for the T-DNA region of interest may be transiently provided by one of the precursor vectors, pICH11150 (FIG. 4). Because of the irreversibility of the reactions catalyzed by PhiC31 integrase, said integrase can also be constitutively expressed by a genetically engineered plant or plant cell.

Many different site-specific recombinases/integrases that can be used for practicing this invention are known in the art. Suitable recombinases/recombination site systems include inter alia the Cre-Lox system from bacteriophage P1 (Austin et al., 1981, *Cell*, 25, 729-736), the Flp-Frt system from *Saccharomyces cerevisiae* (Broach et al., 1982, *Cell*, 29, 227-234), the R-RS system from *Zygosaccharomyces rouxii* (Araki et al., 1985, *J. Mol. Biol.*, 182, 191-203), the integrase from the *Streptomyces* phage PhiC31 (Thorpe & Smith, 1998, *Proc. Natl. Acad. Sci.*, 95, 5505-5510; Groth et al., 2000, *Proc. Natl. Acad. Sci.*, 97, 5995-6000), and resolvases. In addition, other methods of DNA rearrangement are contemplated to be within the scope of the present invention. Other DNA modification enzyme systems can all be used to generate related but functionally distinct DNA sequences of interest inside of a wild-type or a genetically engineered plant cell: restriction endonuclease, transposase, general or specific recombinase, etc. The use of site-specific recombinases with irreversible mode of action is preferred in this invention, as this allows to create a stable recombination product containing said DNA sequence of interest with a predictable structure.

The choice of a suitable promoter to drive expression of the recombinase is of particular value, as it directly affects the performance of the process of the invention, e.g efficiency of assembly of the T-DNA regions and recovery of desired primary transformants in the plant species of choice. The combination of vector pICH15850 carrying a 5' end of the BAR gene (FIG. 14) with different complementing vectors (e.g. pICH15820, pICH17320, or 17330) produces different results in different plant species. For example, the *Arabidopsis* actin2 promoter performs better in *Arabidopsis* than in tobacco, while the promoter of the *Arabidopsis* gene HSP81.1 gives similarly good results in both plants, *Arabidopsis* and tobacco.

Different methods may be used for providing a plant cell or a plant with said at least two different vectors (precursor vectors). Said vectors may be transformed into plant cells by a Ti-plasmid vector carried by *Agrobacterium* (U.S. Pat. No. 5,591,616; U.S. Pat. No. 4,940,838; U.S. Pat. No. 5,464,763) or particle or microprojectile bombardment (U.S. Pat. No. 5,100,792; EP 00444882B1; EP 00434616B1). Other plant transformation methods can also be used like microinjection (WO 09209696; WO 09400583A1; EP 175966B1), electroporation (EP00564595B1; EP00290395B1; WO 08706614A1) or PEG-mediated transformation of protoplasts etc. The choice of precursor vector delivery, like transformation protocols, depends on the plant species to be transformed. For example, microprojectile bombardment is generally preferred for monocot transformation, while for dicots, *Agrobacterium*-mediated transformation gives better results in general.

In the embodiment described above, we used *Agrobacterium*-mediated delivery of vector precursors into *Nicotiana* cells. However, the heterologous DNA may be introduced into the plants in accordance with any of the standard techniques suitable for stable transformation of plant species of interest. Transformation techniques for dicotyledons are well known in the art and include *Agrobacterium*-based techniques and techniques which do not require *Agrobacterium*. Non-*Agrobacterium* techniques involve the uptake of exogenous genetic material directly by protoplasts or cells. These techniques include PEG or electroporation mediated uptake, particle bombardment-mediated delivery and microinjection. Examples of these techniques are described in Paszkowski et al., EMBO J 3:2717-2722 (1984), Potrykus et al., Mol. Gen. Genet. 199:169-177 (1985), Reich et al., Biotechnology 4:1001-1004 (1986), and Klein et al., Nature 327:70-73 (1987). In each case, the transformed cells are regenerated to whole plants using standard techniques.

*Agrobacterium*-mediated transformation is a preferred technique for the transformation of dicotyledons because of its high transformation efficiency and its broad utility with many different species. The many crop species which may be routinely transformed by *Agrobacterium* include tobacco, tomato, sunflower, cotton, oilseed rape, potato, soybean, alfalfa and poplar (EP 0 317 511 (cotton), EP 0 249 432 (tomato), WO 87/07299 (*Brassica*), U.S. Pat. No. 4,795,855 (poplar)). *Agrobacterium* transformation typically involves the transfer of the binary vector carrying the foreign DNA of interest to an appropriate *Agrobacterium* strain which may depend on the complement of vir genes carried by the host *Agrobacterium* strain either on a co-resident plasmid or chromosomally (Uknes et al., Plant Cell 5:159-169 (1993). The transfer of the recombinant binary vector to *Agrobacterium* may be accomplished by a triparental mating procedure using *E. coli* carrying the recombinant binary vector, a helper *E. coli* strain which carries a plasmid such as pRK2013, which is able to mobilize the recombinant binary vector to the target *Agrobacterium* strain. Alternatively, the recombinant binary vector may be transferred to *Agrobacterium* by DNA transformation (Höfgen & Willmitzer, Nucl. Acids Res. 16, 9877 (1988)).

Transformation of the target plant species by recombinant *Agrobacterium* usually involves co-cultivation of the *Agrobacterium* with explants from the plant following protocols known in the art. Transformed tissue carrying an antibiotic or herbicide resistance marker present between the binary plasmid T-DNA borders may be regenerated on selectable medium.

Preferred transformation techniques for monocots include direct gene transfer into protoplasts using PEG or electroporation techniques and particle bombardment into callus tissue.

The patent applications EP 0 292 435, EP 0 392 225 and WO 93/07278 describe techniques for the preparation of callus and protoplasts of maize, transformation of protoplasts using PEG or electroporation, and the regeneration of maize plants from transformed protoplasts. Gordon-Kamm, et al., Plant Cell 2:603-618 (1990), and Fromm, et al., Biotechnology 11:194-200 (1993), describe techniques for the transformation of elite inbred lines of maize by particle bombardment.

Transformation of rice can also be undertaken by direct gene transfer techniques utilizing protoplasts or particle bombardment. Protoplast-mediated transformation has been described for Japonica-types and Indica-types (Zhange, et al., Plant Cell Rep. 7:739-384 (1988); Shimamoto, et al., Nature 338:274-277 (1989); Datta, et al., Biotechnology 8:736-740 (1990)). Both types are also routinely transformable using particle bombardment (Christou, et al., Biotechnology 9:957-962 (1991)). *Agrobacterium*-mediated rice transformation is also applicable (Chan et al., 1993, *Plant Mol. Biol.*, 22, 491-506).

EP 0 332 581 describes techniques for the generation, transformation and regeneration of Pooideae protoplasts. Furthermore, wheat transformation is described by Vasil, et al., Biotechnology 10:667-674 (1992) using particle bombardment into cells of type C long-term regenerable callus. Vasil, et al., Biotechnology 11:1553-1558 (1993) and Weeks, et al., Plant Physiol. 102:1077-1084 (1993) describe particle bombardment of immature embryos and immature embryo-derived callus.

Transformation of monocot cells such as *Zea mays* may be achieved by bringing the monocot cells into contact with a multiplicity of needle-like bodies on which these cells may be impaled, causing a rupture in the cell wall thereby allowing entry of transforming DNA into the cells (see U.S. Pat. No. 5,302,523). Transformation techniques applicable to both monocots and dicots are also disclosed in the following U.S. Pat. No. 5,240,855 (particle gun); U.S. Pat. No. 5,204,253 (cold gas shock accelerated microprojectiles); U.S. Pat. No. 5,179,022 (biolistic apparatus); U.S. Pat. Nos. 4,743,548 and 5,114,854 (microinjection); and U.S. Pat. Nos. 5,149,655 and 5,120,657 (accelerated particle mediated transformation); U.S. Pat. No. 5,066,587 (gas driven microprojectile accelerator); U.S. Pat. No. 5,015,580 (particle-mediated transformation of soy bean plants); U.S. Pat. No. 5,013,660 (laser beam-mediated transformation); U.S. Pat. Nos. 4,849,355 and 4,663,292.

Transgenic plant cells or plant tissue transformed by one of the methods described above may then be grown to full plants in accordance with standard techniques. Transgenic seeds can be obtained from transgenic flowering plants in accordance with standard techniques. Likewise, non-flowering plants such as potato and sugar beets can be propagated by a variety of known procedures. See, e.g., Newell et al. Plant Cell Rep. 10:30-34 (1991) (disclosing potato transformation by stem culture).

The assembly of a DNA sequence of interest in planta from precursor vectors can be greatly facilitated by the presence of helper (auxiliary) sequences A' and B' (FIG. 1A, II) which are preferably absent in the assembled DNA sequence of interest AB (FIG. 1A, II). These helper sequences may end up in recombination products that do not contain said DNA sequence of interest. Such auxiliary sequences can provide genes of interest that are necessary for assembly of the DNA sequence of interest (e.g. recombinases), removal of transformants carrying a precursor vector stably integrated into chromosomal DNA (e.g. using counter-selectable marker genes), transiently provide for gene products necessary for early stages of tissue culture (e.g. genes responsible for biosynthesis of phytohormones), etc.

In one preferred embodiment of the invention, the generation of a DNA sequence of interest for monocotyledonous plants (FIG. 9) from precursor vectors (FIG. 8) is described. Said precursor vectors may contain two types of auxiliary sequences—one may provide for the site-specific integrase PhiC31 and another may provide for isopentenyl transferase (IPT) altering endogenous cytokinins in affected plant cells (Medford et al., 1989, *Plant Cell*, 1, 403-413). The IPT gene, in an addition to being used as inducer of axillary bud formation, can be used as selectable marker gene causing plant morphological abnormality, once stably integrated into chromosomal DNA (Ebinuma et al., 1997, *Proc. Natl. Acad. Sci. USA*, 94, 2117-2121). In this embodiment, the IPT gene can be used as counter-selectable marker allowing for identification and removal of the transformed plant tissues containing precursor vector sequences stably integrated into genomic DNA. FIG. 18 shows tobacco regenerants that contain the IPT gene in T-DNA. They are clearly distinct from the regenerants not having the IPT gene. Other examples of counter-selectable markers (CSM) for use in the present invention are the gene coding for conditionally lethal cytosine desaminase (codA) (Gleave et al., 1999, *Plant Mol. Biol.*, 40, 223-235) or a gene coding for bacterial cytochrome P-450 (O'Keefe et al., 1994, *Plant Physiol.*, 105, 473-482).

In another preferred embodiment, a mixture of more than two different precursor vectors is used for assembling various DNA sequences of interest. Said DNA sequences of interest may be the result of random site-specific recombination events between two sets of precursor vectors (set $A_n$ and set $B_n$, FIG. 1B, I). Actually, a set of DNA sequences of interest of the type $A_nB_n$ may be generated in a plant cell by site-specific recombination of a set of precursor vectors ($A_1$, $A_2$, ..., $A_n$) with a set of precursor vectors ($B_1, B_2, \ldots, B_n$), wherein n is the number of precursor vectors of type A or type B. At least three different precursor vectors are needed to endow the cell with at least two different DNA sequences of interest. The number of all possible combinations of DNA sequences of interest that can be assembled from the plurality of precursor vectors A and the plurality of precursor vectors B may be calculated by multiplying the number of precursor vectors of type A times number of precursor vectors of type B.

Examples for nucleic acid sequences represented as part of A or B and joint together by site-specific recombination may be coding sequences or parts thereof or any genetic elements. Herein, such a genetic element (or regulatory element) may be any DNA element that has a distinct genetic function on DNA or RNA level, said function is other than coding for a structural part of a gene. Examples include: transcriptional enhancers, promoters or parts thereof, translational enhancers, recombination sites, transcriptional termination sequences, internal ribosome entry sites (IRESes), restriction sites, autonomously replicating sequences or origins of replications.

In this invention, the recombination product containing said DNA sequence of interest can consist of components of more than two precursor vectors. In FIG. 1B, II, the assembly of such a DNA sequence of interest containing sequence portions from three different precursor vectors A, B and C, is shown. However, for efficient assembly of said DNA sequence of interest, the use of more than one type of recombinase and/or integrases may be required.

The assembly of a DNA sequence of interest for stable integration into a chromosome of a plant cell allows for the selection of plant cells with said DNA sequence of interest integrated into the chromosomal DNA. One possible mechanisms of selection for said DNA sequence of interest is the assembly of a functional selectable marker gene as is described in detail in examples 1-3 and shown in general in FIG. 10. The use of a counter-selectable marker gene (CSM) in all precursor vectors (FIGS. 10 and 11) allows for easy removal of plant cells carrying precursor vectors stably integrated into chromosomal DNA. In some cases, the assembly of a DNA sequence of interest together with the assembly of a functional gene of interest might be an advantage, e. g. when the gene of interest is toxic for bacterial cells. The selectable marker in such cases can be a part of a bicistronic construct under control of an IRES element (FIG. 11). The site-specific recombination of precursor vectors (A and B in FIG. 11) may lead to the formation of DNA sequence of interest carrying the functional bicistronic construct with the gene of interest followed by an IRES-controlled selectable marker gene. The use of IRES elements in plants is known in the prior art (WO9854342; WO0246440; Dorokhov et al., 2002, *Proc. Natl. Acad. Sci. USA*, 99, 5301-5306) and can be routinely practiced in combination with the present invention.

The assembly of complex vectors in planta from precursor vectors that are of simpler structure can be a further advantage, allowing to avoid complex cloning steps and/or manipulation with unstable DNA structures in bacterial cells. The assembly of the DNA sequence of interest for generating different derivative vectors in allelic position toward each other is shown in FIG. 12. Said DNA sequence of interest (FIG. 12,C) stably integrated into the plant chromosomal DNA can be further exposed to a transposase of choice (Ac or Spm, FIG. 13), allowing to remove the targeted sequences (flanked by Ds sequences for Ac or dSpm sequences for Spm). The final derivative vectors B and C (FIG. 13) are allelic in relation to each other and encode different parts of a gene of interest (GOI) that can be assembled through intein-mediated trans-splicing. This approach addresses biosafety issues, e.g. the control of transgene segregation, as the two fragments of the same gene providing for a trait of interest would always segregate to different gametes due to their allelic location. Details on biologically/environmentally safe transgenic plants having fragments of a transgene in allelic relation can be found in WO03/102197.

The transgenic plants or plant cells produced according to the invention may be used for many different purposes, some of which have been mentioned above. In a further application, the DNA sequence of Interest assembled in planta may in turn also be used as a precursor vector for downstream processes. Said DNA sequence of interest may e.g. be induced to form an extrachromosomal DNA like an independently maintained episomal vector. This inducing may e.g. be achieved by crossing a transgenic plant of the invention carrying said DNA sequence of interest with another plant that provides a factor capable of exerting the inducing function or triggering the formation of said extrachromosomal/episomal DNA. Alternatively, the formation of such an episomal DNA can be caused e.g. by transient expression of a factor (e.g. transposase, viral replicase, etc.) capable of triggering formation of the extrachromosomal/episomal DNA from said DNA sequence of interest. Said episomal DNA may be capable of further reintegration (e.g. it may be or have properties of a transposable element) or be capable of independent maintenance during cell divisions (derivative of DNA viral vector).

The present invention is preferably carried out with higher, multi-cellular plants. Preferred plants for the use in this invention include any plant species with preference given to agronomically and horticulturally important species. Common crop plants for the use in present invention include alfalfa, barley, beans, canola, cowpeas, cotton, corn, clover, lotus, lentils, lupine, millet, oats, peas, peanuts, rice, rye, sweet clover, sunflower, sweetpea, soybean, sorghum triticale, yam beans, velvet beans, vetch, wheat, wisteria, and nut plants. The plant species preferred for practicing of this invention are including but not restricted to: Representatives of Gramineae, Compositeae, Solanaceae and Rosaceae.

Additionally, preferred species for use the invention, as well as those specified above, plants from the genera: *Arabidopsis, Agrostis, Allium, Antirrhinum, Apium, Arachis, Asparagus, Atropa, Avena, Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza, Panicum, Pelargonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setaria, Sinapis, Solanum, Sorghum, Stenotaphrum, Theobroma, Trifolium, Trigonella, Triticum, Vicia, Vigna, Vitis, Zea*, and the Olyreae, the Pharoideae and many others.

Within the scope of this invention the plant species, which are not included into the food or feed chain are specifically preferred for pharmaceutical and technical proteins production. Among them, *Nicotiana* species are the most preferred, as the species easy to transform and cultivate with well developed expression vectors (especially viral vectors) systems.

Genes of interest, their fragments (functional or non-functional) and their artificial derivatives that can be expressed in plants or plants cells using the present invention include, but are not limited to: starch modifying enzymes (starch synthase, starch phosphorylation enzyme, debranching enzyme, starch branching enzyme, starch branching enzyme II, granule bound starch synthase), sucrose phosphate synthase, sucrose phosphorylase, polygalacturonase, polyfructan sucrase, ADP glucose pyrophosphorylase, cyclodextrin glycosyltransferase, fructosyl transferase, glycogen synthase, pectin esterase, aprotinin, avidin, bacterial levansucrase, *E. coli* gIgA protein, MAPK4 and orthologues, nitrogen assimilation/metabolism enzyme, glutamine synthase, plant osmotin, 2S albumin, thaumatin, site-specific recombinase/integrase (FLP, Cre, R recombinase, Int, SSVI Integrase R, Integrase phiC31, or an active fragment or variant thereof, isopentenyl transferase, Sca M5 (soybean calmodulin), coleopteran type toxin or an insecticidally active fragment, ubiquitin conjugating enzyme (E2) fusion proteins, enzymes that metabolise lipids, amino acids, sugars, nucleic acids and polysaccharides, superoxide dismutase, inactive proenzyme form of a protease, plant protein toxins, traits altering fiber in fiber producing plants, Coleopteran active toxin from *Bacillus thuringiensis* (Bt2 toxin, insecticidal crystal protein (ICP), CryIC toxin, delta endotoxin, polyopeptide toxin, protoxin etc.), insect specific toxin AaIT, cellulose degrading enzymes, E1 cellulase from *Acidothermus celluloticus*, lignin modifying enzymes, cinnamoyl alcohol dehydrogenase, trehalose-6-phosphate synthase, enzymes of cytokinin metabolic pathway, HMG-CoA reductase, *E. coli* inorganic pyrophosphatase, seed storage protein, *Erwinia herbicola* lycopen synthase, ACC oxidase, pTOM36 encoded protein, phytase, ketohydrolase, acetoacetyl CoA reductase, PHB (polyhydroxybutanoate) synthase, acyl carrier protein, napin, EA9, non-higher plant phytoene synthase, pTOM5 encoded protein, ETR (ethylene receptor), plastidic pyruvate phosphate dikinase, nematode-inducible transmembrane pore protein, trait enhancing photosynthetic or plastid function of the plant cell, stilbene synthase, an enzyme capable of hydroxylating phenols, catechol dioxygenase, catechol 2,3-dioxygenase, chloromuconate cycloisomerase, anthranilate synthase, *Brassica* AGL15 protein, fructose 1,6-biphosphatase (FBPase), AMV RNA3, PVY replicase, PLRV replicase, potyvirus coat protein, CMV coat protein, TMV coat protein, luteovirus replicase, MDMV messenger RNA, mutant geminiviral replicase, *Umbellularia californica* C12:0 preferring acyl-ACP thioesterase, plant C10 or C12:0 preferring acyl-ACP thioesterase, C14:0 preferring acyl-ACP thioesterase (luxD), plant synthase factor A, plant synthase factor B, D6-desaturase, protein having an enzymatic activity in the peroxysomal b-oxidation of fatty acids in plant cells, acyl-CoA oxidase, 3-ketoacyl-CoA thiolase, lipase, maize acetyl-CoA-carboxylase, 5-enolpyruvylshikimate-3-phosphate synthase (EPSP), phosphinothricin acetyl transferase (BAR, PAT), CP4 protein, ACC deaminase, protein having posttranslational cleavage site, DHPS gene conferring sulfonamide resistance, bacterial nitrilase, 2,4-D monooxygenase, acetolactate synthase or acetohydroxyacid synthase (ALS, AHAS), polygalacturonase, Taq polymerase, bacterial nitrilase, many other enzymes of bacterial or phage including restriction endonucleases, methylases, DNA and RNA ligases, DNA and RNA polymerases, reverse trascryptases, nucleases (Dnases and RNAses), phosphatases, transferases etc.

The present invention also can be used for the purpose of molecular farming and purification of commercially valuable and pharmaceutically important proteins including industrial enzymes (cellulases, lipases, proteases, phytases etc.) and fibrous proteins (collagen, spider silk protein, etc.). Human or animal health protein may be expressed and purified using described in our invention approach. Examples of such proteins of interest include inter alia immune response proteins (monoclonal antibodies, single chain antibodies, T cell receptors etc.), antigens including those derived from pathogenic microorganisms, colony stimulating factors, relaxins, polypeptide hormones including somatotropin (HGH) and proinsulin, cytokines and their receptors, interferons, growth factors and coagulation factors, enzymatically active lysosomal enzyme, fibrinolytic polypeptides, blood clotting factors, trypsinogen, a1-antitrypsin (AAT), human serum albumin, glucocerebrosidases, native cholera toxin B as well as function-conservative proteins like fusions, mutant versions and synthetic derivatives of the above proteins.

The above proteins and others can optimised for a desired purpose by introducing random mutations into their coding sequence or by gene shuffling methods. Screening for a protein having optimised properties for the desired purpose may then be done using the process of the present invention.

EXAMPLES

The following examples are presented to illustrate the present invention. Modifications and variations may be made without departing from the spirit and scope of the invention.

Example 1

Vector Design for the Stable Transformation of Dicotyledonous Plants with Split BAR Gene Design of pICH11150

This construct was done on the basis of binary vector pICBV-19 (FIG. 2). As a first step of cloning, the target BsaI restriction sites for the intron insertion were introduced into the BAR gene (construct pICH10605, FIG. 2). The BsaI enzyme cuts DNA outside of the recognition site making 4 nucleotides overhang. In the case of pICH10605, the BsaI enzyme was used to introduce splicing acceptor and donor sites for the consequent intron insertion. As a next step, PCR fragment amplified on pICH7410 (FIG. 3) construct with oligos int-ad-9 (5'-tttttggtc cgacctgcaa caataagaac aaaaagtcat aaatt-3'; SEQ ID NO: 1) and attbpr11 (5'-tttaagcttg agctctttcc taggctcgaa gccgcggtgc gggtg-3'; SEQ ID NO: 2) was inserted into pICH10605 using BsaI and HindIII restriction sites. The PCR fragment containing AttB and 3' part of intron as well as AvrII and SacI restriction sites replaced the GUS expression cassette and 5'part of BAR expression cassette. The T-DNA part of the resulting construct (pICH11140, FIG. 4) contained the 3' part of BAR expression cassette: AttB, 3'part of the intron, 3' part of BAR-gene and OCS terminator as well as AvrII and SacI restriction sites. As a final step of 3' construct cloning, a PhiC31 integrase expression cassette containing Arabidopsis actin 2 promoter, PhiC31 integrase and NOS terminator was introduced into pICH11140 using AvrII and SacI restriction sites. The final construct pICH11150, containing 3' end of BAR gene with AttB, recombination site together with the 3' end of the intron, as well as PhiC31 integrase expression cassette is shown in FIG. 4.

Design of pICH11170

This construct was done on the basis of binary vector pICBV-16 (FIG. 5). The PCR fragment amplified from pICH8430 (FIG. 5) with oligos int-ad-10 (5'-tttaagcttg aattcttttg gtctcaggta agtttcattt tcataattac aca-3'; SEQ ID NO: 3) and attppr14 (5'-tttttcaatt ggagctccta cgcccccaac tgagagaac-3'; SEQ ID NO: 4) was cut with HindIII and MfeI restriction enzymes and introduced into pICBV-16 digested with HindIII and EcoRI. PCR fragment containing 5' part of intron and AttP as well as BsaI and EcoRI restriction sites replaced the GUS expression cassette in intermediate construct pICH11160 (FIG. 6). As the final step of the cloning, EcoRI/BsaI fragment of pICH10605 (FIG. 2) containing a NOS promoter and 5' part of BAR gene was inserted into pICH11160. The T-DNA region of the final construct pICH11170 is shown in FIG. 6.

Further vectors for use in the invention are described in the following.

Design of pICH17330

The AvrII/NcoI DNA fragment containing the Arabidopsis Hsp81.1 promoter and fragment of PhiC31 integrase ORF was transferred into the pICH15820 (FIG. 14) construct linearised with AvrII and NcoI enzymes yielding pICH 17330 (FIG. 15).

Design of pICH17320

The Spe/NcoI DNA fragment containing the complete Spm promoter and the fragment of PhiC31 integrase ORF was transferred into pICH15820 (FIG. 14) construct linearised with AvrII and NcoI enzymes yielding pICH17320 (FIG. 15).

Design of pICH15850

The NotI/SacI fragment of pICH11170 (FIG. 6) was fused with adapters adipt1 (5' ggccgcttt tatgcattt tttgagctct cgcgaggatc ctagct 3'; SEQ ID NO: 5) and adipt2 (5' aggatcctcg cgagagctca aaaaatgcat aaaaagc 3'; SEQ ID NO: 6) that destroyed the original SacI site and introduced BamHI, SacI and NsiI sites, producing pICH15830 (FIG. 16). For pICH15840 cloning, the NotI/NsiI fragment of pICBV2 (FIG. 16) was transferred to the pICH15830 (FIG. 16) construct, reintroducing T-DNA left border region which was excised in the first step of cloning. The BamHI/SacI fragment of pICH15820 (FIG. 14) containing complete IPT gene was transferred to pICH15840, resulting in pICH15850 (FIG. 14).

Design of pICH15820

The cloning of 3' split-BAR construct with isopenthenyl transferase (IPT) gene (pICH15820) comprised several steps. In the pICH13630 construct (FIG. 17,A), adapter adipt3/adipt4 that destroyed original AvrII and SacI sites and introduced SacI and AvrII sites in reverse orientation replaced AvrII/SacI fragment. In addition, this adapter introduced SpeI and XhoI sites for the insertion of IPT gene (pICH15760, FIG. 17, A). The AvrII/SacI fragment containing a PhiC31 integrase expression cassette (Arabidopsis actin 2 promoter-PhiC31 integrase ORF with C-terminal nuclear localization signal-nos terminator) was transferred from pICH10881 to pICH15760 resulting in pICH15770 (FIG. 17, B)

Isopenthenyl transferase (IPT) gene (including original promoter and terminator regions) of *Agrobacterium* strain C58 (appr. 2 kb) was amplified by PCR as 4 fragments flanked by BsaI restriction sites. PCR fragments were subcloned into pGEM-T vectors and then isolated using BsaI enzyme having its recognition site outside of the digestion site. This allows to create 4 bp overhangs with any nucleotide sequence enabled to assemble the entire IPT gene and insert it into the pICH15770 (FIG. 17) contruct linearised with XhoI/SpeI in one ligation step. This cloning resulted in pICH15820 (FIG. 14).

Example 2

*Agrobacterium*-Mediated Transformation of the Dicotyledonous Plant *Nicotiana tabacum* (cv Petit Havana) and *Arabidopsis thaliana* with in planta Assembled T-DNA Region The constructs pICH11150 and pICH11170 were immobilized into *A. tumefaciens* (GV3101) and used for *Agrobacterium*-mediated leaf discs transformation of *Nicotiana* plants (Horsh et al., 1985, *Science*, 227, 1229-1231) using 10 mg/L of phosphinothricin (PPT) as selectable marker. *Arabidopsis thaliana* plants were transformed using a vacuum infiltration protocol (Bechtold et al., 1993, *C. R. Acad. Sci. Paris Life Sci.* 316, 1194-1199). Phosphinothricine-resistant ($PPT^R$) transformants were selected by spraying one-week-old plantlets with a 2.5 ml/L of Harvest™ (Agrevo) solution (active ingredient glufosinate, commercially available PPT-analogous compound).

Regenerated tobacco plants and selected *A. thaliana* primary transformants were PCR analysed for the presence of an in planta assembled T-DNA region stably integrated into chromosomal DNA (FIG. 7) and for the absence of the T-DNA regions of pICH11150 and pICH11170. PCR analysis demonstrated that approximately 8% of all *Arabidopsis* transformants contained the desired T-DNA region (FIG. 7) without co-integrated T-DNA regions of pICH11150 and pICH11170. The same analysis of tobacco regenerants revealed a significantly lower frequency of plants with desired genotype than observed with *Arabidopsis*—less than 0.1%. Similar results described above were obtained with the complementing pair of constructs pICH15820 and pICH15850 (FIG. 14). However, there were no primary transformants resulting from co-integration (and restoration of BAR activity by intron formation) of said T-DNA regions, but only from site-specific recombination. This might be explained by the presence of a large region separating the 3' and 5' parts of introns of co-integrated T-DNAs. New set of constructs using integrase under control of different promoters (either *Zea mays* Spm transposase (pICH17320, FIG. 15), or *Arabidopsis* heat shock protein Hsp81.1 (pICH17330, FIG. 15) was generated. These vectors in combination with complementary vector pICH15850 (FIG. 14) showed much better results than vector pICH15820 (FIG. 14). For example, the frequency of tobacco transformants carrying correctly recombined T-DNA regions without co-integrated T-DNAs were approx 10% or more depending on experiments. This demonstrates that the efficiency of the process can be affected by controlling the efficiency of integrase expression and can be adjusted to any plant species of interest. The regenerating tobacco phenotypes with and without IPT gene are shown in FIG. 18.

Example 3

Vector Design and *Agrobacterium*-Mediated Transformation of Monocotyledonous Plants with Split BAR Gene For the design of constructs using a split BAR gene to monitor desired T-DNA region assembly in planta, the original constructs pICH11150 and pICH11170 (see EXAMPLE 1) were used. The construct pICH11150 was modified by replacing the *Arabidopsis* actin2 (PACT2-i,) promoter with rice actin1 (PACT1) promoter (McElroy D, et al., 1991, *Mol Gen Genet.*, 231, 150-160) yielding construct pICH12022 (FIG. 8). The construct pICH11170 was modified by replacing the nopaline synthase promoter (PNOS) driving expression of the BAR gene fragment with the rice actine1 promoter (PACT1) and the NPTII expression cassette with IPT (isopentenyl transferase, Gene Bank Acc. No.: X14410) expression cassette under control of maize ubiquitin gene promoter (PUBQ) (Christensen A H & Quail P H., 1996, *Transgenic Res.*, 5, 213-218) yielding construct pICH12031 (FIG. 8). All manipulations for construct design were performed using standard cloning procedures (Sambrook, Fritsch & Maniatis, 1989, Molecular cloning: A laboratory manual, 2nd ed. Cold Spring Harbor, N.Y.: CSH Laboratory Press).

The line PEN3 of *Pennisetum glaucum* was used for *Agrobacterium*-mediated transformation with plasmids pICH12022 and pICH12031. Aliquotes of *Agrobacterium tumefaciens* AGL1 strain carrying either pICH12022 or pICH12031 were mixed together in equal proportions and used for transformation as described below.

The culture medium included Murashige and Skoog (MS) salts and vitamins: (Reference: Murashige, T. & Skoog, F. A 1962, *Physiol. Plant.*, 15, 473-497) with 2.0 mg/L of 2,4-D, which is 2,4-Dichlorophenoxyacetic acid, 30 g/l sucrose and 0.3% gelrite. Regeneration medium contained a half-strength MS salts and vitamins with 20 g/L maltose, 1 mg/L IAA, 1 mg/L Zeatin and 0.6% gelrite.

Infection medium (IM) contained a half-strength MS salts and vitamins with 2 mg/L 2,4-D, 10 g/L glucose, 60 g/L maltose, 50 mg/L ascorbic acid, 1 g/L MES (2-N-morpholinoethanesulfonic acid) and 40 mg/L Acetosyringone (AS). The pH of the medium was adjusted to 5.2 by 1 N KOH. Cocultivation medium (CM) was same as the IM (excluding ascorbic acid) and was solidified by adding 0.6% gelrite.

Infection medium was filter sterilized, whereas all other media were autoclaved. AS, dissolved in DMSO (400 mg/mL), was added after sterilization.

Agrobacterial cultures (strains AGL1, EHA105, A4 etc.) with the appropriate binary plasmids were grown for 3 days at room temperature on LB2N (LB medium with 2 g/L NaCl and 1.5% agar) plates supplemented with the appropriate antibiotics. Bacteria were scraped from the plates and resuspended in IM in 50-mL falcon tubes. The tubes were fixed horizontally to a shaker platform and shaken at low speed for 4 to 5 h at room temperature. Optical density of the suspension was measured and OD600 was adjusted to 1.0.

Callus pieces were incubated in the Agrobacterial suspension for 3 hours at room temperature and transferred to the gelrite-solidified CM with 60 g/L maltose.

After 3 days of cultivation on CM, the calli were washed five times by half-strength MS medium with 60 g/L sucrose and transferred to the gelrite-solidified CM with 60 g/L sucrose and 5 mg/L phosphinothricin (PPT) and, in some cases, 150 mg/L Timentin. Phosphinothricin-resistant calli developed under selection were plated to the regeneration medium with 5 mg/L PPT.

The regenerating PPT$^R$ plant tissues were initially visually tested for the absence of functional IPT gene causing adventitious formation of shoots in hormone-free media (Ooms et al., 1983, *Theor. Appl. Genet.*, 66, 169-172; Smigocki, A C & Owens, L D., 1989, *Plant Physiol.*, 91, 808-811; Smigocki, A C & Owens, L D. 1988, *Proc. Natl. Acad. Sci. USA*, 85, 5131-5135). Secondary screening for plants carrying in planta assembled T-DNA region (FIG. 9) and for the absence of T-DNA regions from pICH12022 and pICH12031 were carried out by using PCR analysis of PPT$^R$ plant tissue for the presence of integrase PhiC31 and IPT gene sequences.

The invention claimed is:

1. A process of producing transgenic plants or plant cells comprising a chromosome stably transformed with a DNA sequence of interest, said plants or plant cells being capable of expressing a protein of interest from said DNA sequence of interest, said process comprising
  (a) providing a plant cell with at least two different vectors in one step by *Agrobacterium*-mediated delivery, whereby
  (i) said at least two different vectors are adapted to recombine with each other by site-specific recombination in said plant cells between site-specific recombination sites that are present on said at least two different vectors and are compatible with a site-specific recombinase, and wherein step (a) comprises providing said site-specific recombinase by including an expressible sequence coding for said recombinase on a vector of said at least two different vectors, said recombinase being specific for said recombination sites for producing a non-replicating recombination product assembled from said at least two different vectors and containing said DNA sequence of interest,
  (ii) said at least two different vectors are adapted for integrating said DNA sequence of interest into said chromosome,
  (iii) said DNA sequence of interest contains sequence portions from said at least two different vectors, said sequence portions being necessary for expressing said protein of interest from said DNA sequence of interest; and
  (b) selecting plants or plant cells expressing said protein of interest.

2. The process of claim 1, wherein each of said at least two different vectors is provided by a different *Agrobacterium* cell or strain.

3. The process of claim 1, wherein one or all of said at least two different vectors contain(s) a functional cytokinin autonomy gene whereas said DNA sequence of interest is devoid of a functional cytokinin autonomy gene.

4. The process of claim 1, wherein expressibility of said sequence coding for said recombinase is destroyed by said site-specific recombination.

5. The process of claim 1, wherein said at least two different vectors are adapted such that said DNA sequence of interest has T-DNA border sequences that facilitate integration of said DNA sequence of interest into said chromosome.

6. The process of claim 1, wherein said at least two different vectors are adapted such that said DNA sequence of interest contains homology sequences that facilitate integration of said DNA sequence of interest into said chromosome by homologous recombination.

7. The process of claim 1, wherein said at least two different vectors are adapted for introducing said DNA sequence of interest into said chromosome by site-specific integration.

8. The process of claim 1, wherein step (b) further comprises screening for plants or plant cells having said DNA sequence of interest integrated in said chromosome.

9. The process of claim 1, wherein step (b) further comprises screening for cells or plants in which said site-specific recombination between said at least two vectors has occurred.

10. The process of claim 1, wherein said at least two different vectors are adapted such that said DNA sequence of interest contains a selectable marker gene or a sequence that allows in step (b) screening for transformed plants or plant cells containing said DNA sequence of interest.

11. The process of claim 1, wherein a sequence portion of one of said at least two different vectors contains a selectable marker under translational control of an internal ribosome entry site (IRES) element.

12. The process of claim 11, wherein said selectable marker cannot be transcribed in said plant cells from one of said at least two different vectors but is placed by said site-specific recombination under the control of genetic elements allowing transcription of said selectable marker.

13. The process of claim 1, wherein at least one of said at least two different vectors contain a counter-selectable marker gene or another sequence that allows screening against transformed cells containing said vectors.

14. The process of claim 13, wherein said counter-selectable marker gene or said another sequence that allows screening against transformed cells containing said vectors is under translational control of an internal ribosome entry site (IRES) element.

15. The process of claim 1, wherein said expressing comprises intron-mediated cis-splicing.

16. The process of claim 15, wherein
a first vector of said at least two different vectors contains
   a first sequence portion that contains:
      a first part of a sequence coding for the protein to be expressed and, downstream thereof, a 5' part of an intron, and
a second vector of said at least two different vectors contains a second sequence portion that contains:
   a second part of a sequence coding for the protein to be expressed and, upstream thereof, a 3' part of an intron.

17. The process of claim 1, wherein three or more different vectors are provided to said plant cell in step (a) and two or more different transgenic plants or plant cells are produced, said different transgenic plants or plant cells having different DNA sequences of interest integrated in a chromosome.

18. The process of claim 1, wherein said plant cells are provided with two different vectors, and said DNA sequence of interest contains a sequence portion from each of these two vectors.

19. The process of claim 1, comprising the following steps (A) and (B):
(A) providing plants or plant cells with a mixture of
   (i) a set of m primary vectors each having a primary sequence portion selected from the set $a_1, a_2, \ldots, a_m$ and
   (ii) a set of n secondary vectors each having a secondary sequence portion selected from the set $b_1, b_2, \ldots, b_n$, whereby
   m and n are independent of each other and both are integers of >1, said primary vectors and said secondary vectors are adapted such that each member of said set of primary vectors can recombine with every member of said set of n secondary vectors by site-specific recombination for producing recombination products containing different DNA sequences of interest, each DNA sequence of interest comprises a member of said set of primary sequence portions and a member of said set of secondary sequence portions, both said sequence portion members are necessary for expressing said protein of interest from said DNA sequence of interest; and
   said primary vectors and said secondary vectors are adapted to integrate said DNA sequences of interest into a chromosome; and
(B) selecting transformed plants or plant cells expressing said protein of interest from a DNA sequence of interest.

20. The process of claim 1, comprising the following steps (A) and (B):
(A) providing plants or plant cells with a mixture of
   (i) a primary vector having a primary sequence portion $a_1$ and
   (ii) a set of n secondary vectors each having a secondary sequence portion selected from the set $b_1, b_2, \ldots, b_n$, whereby
   n is an integer of >1,
   said primary sequence portion $a_1$ is necessary for expressing the function of a secondary sequence portion $b_1, b_2, \ldots, b_n$,
   said primary vector and said secondary vectors are adapted such that said primary vector can recombine with every member of said set of n secondary vectors by site-specific recombination for producing recombination products containing different DNA sequences of interest of type $a_1b_1, a_1b_2, \ldots, a_1b_n$ or type $b_1a_1, b_2a_1, \ldots, b_na_1$,
   said primary vector and said secondary vectors are adapted to integrate said DNA sequences of type $a_1b_1, a_1b_2, \ldots, a_1b_n$ or type $b_1a_1, b_2a_1, \ldots, b_na_1$ into a chromosome; and
(B) selecting transformed plants or plant cells expressing a protein of interest from a DNA sequence of interest.

21. The process of claim 19, further comprising determining a phenotypic feature of a transformed plant or plant cell selected in step (B) due to a protein encoded by
the primary sequence portion, and/or
the secondary sequence portion, and/or
a combination of the primary sequence portion and the secondary sequence portion.

* * * * *

```
                       SEQUENCE LISTING

<160> NUMBER OF SEQ ID NOS: 8

<210> SEQ ID NO 1
<211> LENGTH: 44
<212> TYPE: DNA
<213> ORGANISM: Artificial Sequence
<220> FEATURE:
<223> OTHER INFORMATION: PCR primer

<400> SEQUENCE: 1
tttttggtcc gacctgcaac aataagaaca aaaagtcata aatt            44

<210> SEQ ID NO 2
<211> LENGTH: 45
<212> TYPE: DNA
<213> ORGANISM: Artificial Sequence
<220> FEATURE:
<223> OTHER INFORMATION: PCR primer

<400> SEQUENCE: 2
tttaagcttg agctctttcc taggctcgaa gccgcggtgc gggtg            45

<210> SEQ ID NO 3
<211> LENGTH: 53
<212> TYPE: DNA
<213> ORGANISM: Artificial Sequence
<220> FEATURE:
<223> OTHER INFORMATION: PCR primer

<400> SEQUENCE: 3
tttaagcttg aattcttttg gtctcaggta agtttcattt tcataattac aca   53

<210> SEQ ID NO 4
<211> LENGTH: 39
<212> TYPE: DNA
<213> ORGANISM: Artificial Sequence
<220> FEATURE:
<223> OTHER INFORMATION: PCR primer

<400> SEQUENCE: 4
tttttcaatt ggagctccta cgcccccaac tgagagaac                   39

<210> SEQ ID NO 5
<211> LENGTH: 45
<212> TYPE: DNA
<213> ORGANISM: Artificial Sequence
<220> FEATURE:
<223> OTHER INFORMATION: adapter

<400> SEQUENCE: 5
ggccgctttt tatgcatttt ttgagctctc gcgaggatcc tagct            45

<210> SEQ ID NO 6
<211> LENGTH: 37
<212> TYPE: DNA
<213> ORGANISM: Artificial Sequence
<220> FEATURE:
<223> OTHER INFORMATION: adapter

<400> SEQUENCE: 6
```

```
aggatcctcg cgagagctca aaaaatgcat aaaaagc                              37

<210> SEQ ID NO 7
<211> LENGTH: 45
<212> TYPE: DNA
<213> ORGANISM: Artificial Sequence
<220> FEATURE:
<223> OTHER INFORMATION: adapter

<400> SEQUENCE: 7
ctagcgagct cttttccta ggactagttc gcgactcgag cagct                      45

<210> SEQ ID NO 8
<211> LENGTH: 37
<212> TYPE: DNA
<213> ORGANISM: Artificial Sequence
<220> FEATURE:
<223> OTHER INFORMATION: adapter

<400> SEQUENCE: 8
gctcgagtcg cgaactagtc ctaggaaaaa gagctcg                              37
```